United States Patent [19]

Murata et al.

[11] Patent Number: 5,286,721

[45] Date of Patent: * Feb. 15, 1994

[54] 1-AZABICYCLO[3.2.0]HEPT-2-ENE-2-CARBOXYLIC ACID COMPOUNDS

[75] Inventors: Masayoshi Murata; Toshiyuki Chiba, both of Osaka; Hideo Tsutsumi, Toyonaka; Kohji Hattori, Nagoya; Satoru Kuroda, Ikeda; Hiroaki Ohtake, Suita; Fumiyuki Shirai, Osaka, all of Japan

[73] Assignee: Fujisawa Pharmaceutical Co., Ltd., Osaka, Japan

[ * ] Notice: The portion of the term of this patent subsequent to Apr. 7, 2009 has been disclaimed.

[21] Appl. No.: 853,746

[22] PCT Filed: Oct. 14, 1991

[86] PCT No.: PCT/JP91/01394

§ 371 Date: Jun. 12, 1992

§ 102(e) Date: Jun. 12, 1992

[87] PCT Pub. No.: WO92/06978

PCT Pub. Date: Apr. 30, 1992

[30] Foreign Application Priority Data

Oct. 15, 1990 [GB] United Kingdom ............... 9022309

[51] Int. Cl.$^5$ ............................................. C07D 477/00
[52] U.S. Cl. ....................................... 514/210; 540/302
[58] Field of Search ......................... 514/210; 540/302

[56] References Cited

U.S. PATENT DOCUMENTS

| | | |
|---|---|---|
| 4,260,627 | 4/1981 | Christensen et al. . |
| 4,267,188 | 5/1981 | Cama et al. . |
| 4,348,320 | 9/1982 | Bouffard et al. . |
| 4,465,632 | 8/1984 | Christensen et al. . |
| 4,517,127 | 5/1985 | Yoshioka et al. . |
| 4,543,257 | 9/1985 | Cama et al. . |
| 4,740,507 | 4/1988 | Sugimura et al. . |
| 5,102,877 | 4/1992 | Murata et al. ............. 540/302 |

FOREIGN PATENT DOCUMENTS

| | | |
|---|---|---|
| 0010316 | 4/1980 | European Pat. Off. . |
| 0010317 | 4/1980 | European Pat. Off. . |
| 0072710 | 2/1983 | European Pat. Off. . |
| 0111286 | 6/1984 | European Pat. Off. . |
| 0184843 | 6/1986 | European Pat. Off. . |
| 0289801 | 11/1988 | European Pat. Off. . |
| 0394991 | 10/1990 | European Pat. Off. . |

OTHER PUBLICATIONS

Greene et al, Protective Groups in Organic Synthesis, Wiley and Sons, 1991, pp. 87–90, 229–230, 232–233.

*Primary Examiner*—Marianne M. Cintins
*Assistant Examiner*—Rebecca Coole
*Attorney, Agent, or Firm*—Oblon, Spivak, McClelland, Maier & Neustadt

[57] ABSTRACT

1-Azabicyclo[3.2.0]hept-2-ene-2-carboxylic acid compounds of the formula:

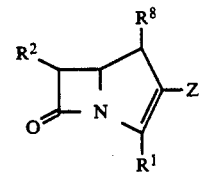

in which $R^1$ is carboxy, COO— or protected carboxy, $R^2$ is hydroxy(lower)alkyl or protected hydroxy(lower)alkyl, $R^8$ is hydrogen or lower alkyl, Z is a group of the formula:

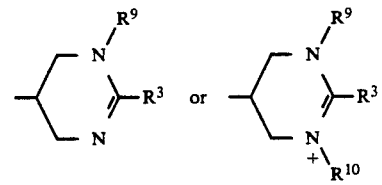

wherein $R^3$ is hydrogen; lower alkyl or lower alkenyl, each of (Abstract continued on next page.)

which is optionally substituted by the group consisting of lower alkoxy, carbamoyl, hydroxy, halogen, mono-(or di)(lower)alkylcarbamoyl, mono(or di)(lower)alkenylcarbamoyl, mono(or bis)[hydroxy(lower)alkyl]-carbamoyl, optionally substituted cyclic-aminocarbonyl, acylamino, ureido, optionally substituted heterocyclic-carbonylamino, carbamoyloxy, mono(or di)(lower)alkylcarbamoyloxy, lower alkylthio, halo(lower)alkylthio, optionally substituted heterocyclicthio, optionally substituted heterocyclic group, optionally substituted aryl, and acyl;

$R^9$ is hydrogen or lower alkyl, and $R^{10}$ is lower alkyl, or pharmaceutically acceptable salts thereof, which is useful as an antimicrobial agent.

9 Claims, No Drawings

1-AZABICYCLO[3.2.0]HEPT-2-ENE-2-CARBOXYLIC ACID COMPOUNDS

The present invention relates to novel 1-azabicyclo[3.2.0]hept-2-ene-2-carboxylic acid compounds and pharmaceutically acceptable salts thereof.

More particularly, it relates to novel 1-azabicyclo[3.2.0]hept-2-ene-2-carboxylic acid compounds and pharmaceutically acceptable salts thereof, which have antimicrobial activity.

INDUSTRIAL APPLICABILITY

Accordingly, the object of the present invention is to provide novel 1-azabicyclo[3.2.0]hept-2-ene-2-carboxylic acid compounds and pharmaceutically acceptable salts thereof, which are highly active against a number of pathogenic microorganisms and are useful as antimicrobial agents.

DISCLOSURE OF INVENTION

The object 1-azabicyclo[3.2.0]hept-2-ene-2-carboxylic acid compounds are novel and can be represented by the following general formula:

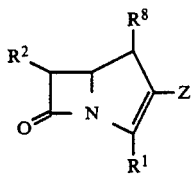

in which
$R^1$ is carboxy, COO— or protected carboxy,
$R^2$ is hydroxy(lower)alkyl or protected hydroxy(lower)alkyl,
$R^8$ is hydrogen or lower alkyl,
Z is a group of the formula:

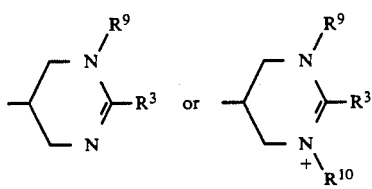

wherein
$R^3$ is hydrogen; lower alkyl or lower alkenyl, each of which is optionally substituted by the group consisting of lower alkoxy, carbamoyl, hydroxy, halogen, mono-(or di)(lower)alkylcarbamoyl, mono(or di)(lower)alkenylcarbamoyl, mono(or bis)-[hydroxy(lower)alkyl]-carbamoyl, optionally substituted cyclic-aminocarbonyl, acylamino, ureido, optionally substituted heterocyclic-carbonylamino, carbamoyloxy, mono(or di)(lower)alkylcarbamoyloxy, lower alkylthio, halo(lower)alkylthio, optionally substituted heterocyclicthio, optionally substituted heterocyclic group, optionally substituted aryl, and acyl;
$R^9$ is hydrogen or lower alkyl, and
$R^{10}$ is lower alkyl,
or pharmaceutically acceptable salts thereof.

Suitable pharmaceutically acceptable salts of the object compound (I) are conventional non-toxic salts and may include;

a salt with a base such as an inorganic base salt, for example, an alkali metal salt (e.g. sodium salt, potassium salt, etc.), an alkaline earth metal salt (e.g. calcium salt, magnesium salt, etc.), an ammonium salt, an organic base salt, for example, an organic amine salt (e.g. triethylamine salt, pyridine salt, picoline salt, ethanolamine salt, triethanolamine salt, dicyclohexylamine salt, N,N'-dibenzylethylenediamine salt, etc.);

a salt with an acid such as inorganic acid addition e.g. hydrochloride, hydrobromide, sulfate, phosphate, etc.), an organic acid addition salt (e.g. formate, acetate, trifluoroacetate, maleate, tartrate, methanesulfonate, benzenesulfonate, etc.);

a salt with a basic or acidic amino acid (e.g. arginine, aspartic acid, glutamic acid, etc.); intermolecular quaternary salt and the like.

Such intermolecular quaternary salt can be prepared when $R^3$ is, for example, pyridyl(lower)alkyl (e.g. 3-pyridylmethyl, etc.) or imidazolyl(lower)alkyl (e.g. imidazol-1-ylmethyl, etc.) and the ring nitrogen atom is further substituted by a suitable substituent such as lower alkyl (e.g. methyl, etc.). In such a case preferable counter anion may be halide (e.g. chloride, etc.).

In the object compound (I) and the intermediary compounds mentioned below, it is to be understood that there may be one or more stereo-isomeric pair(s) such as optical isomers due to asymmetric carbon atom(s), and such isomers are also included within the scope of the present invention.

According to the present invention, the object compound (I) or pharmaceutically acceptable salts thereof can be prepared by the processes as illustrated by the following reaction schemes.

Process 1:

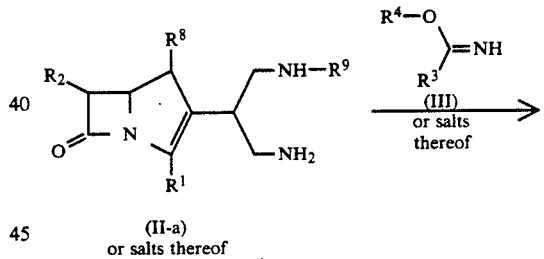

(II-a)
or salts thereof

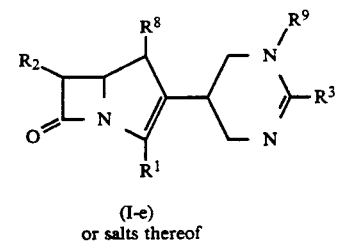

(I-e)
or salts thereof

Process 2:

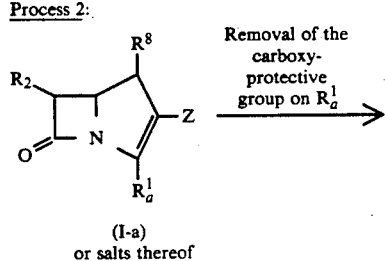

(I-a)
or salts thereof

3
-continued

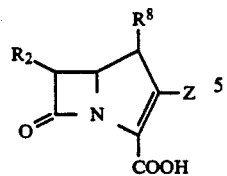

(I-b)
or salts thereof

Process 3:

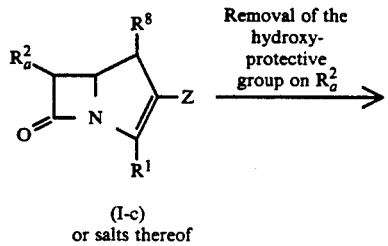

(I-c)
or salts thereof

Process 4:

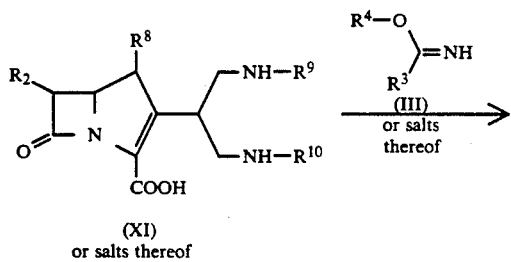

(XI)
or salts thereof

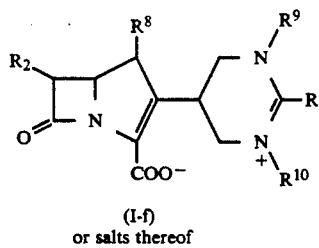

(I-f)
or salts thereof

Process 5:

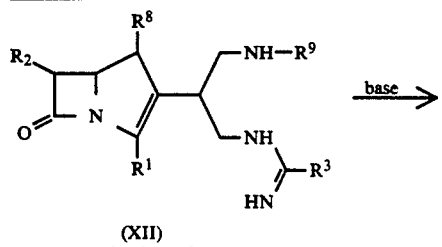

(XII)
or salts thereof

4
-continued

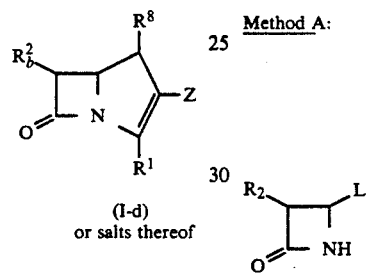

(I-e)
or salts thereof in which
$R^1$, $R^2$, $R^3$, $R^8$, $R^9$, $R^{10}$ and Z are each as defined above,
$R_a^1$ is protected carboxy,
$R_a^2$ is protected hydroxy(lower)alkyl,
$R_b^2$ is hydroxy(lower)alkyl, and
$R^4$ is lower alkyl or ar(lower)alkyl.

The starting compounds used in the above Processes may be new and can be prepared, for example, by the methods as shown in the following.

Method A:

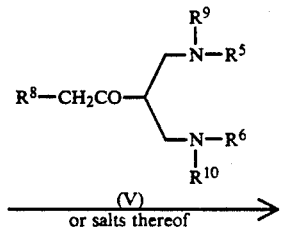

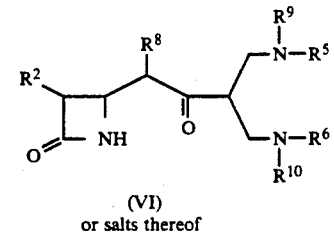

(VI)
or salts thereof

Method B:

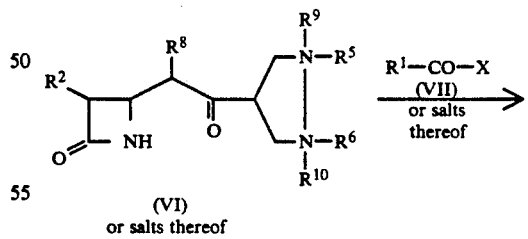

(VI)
or salts thereof

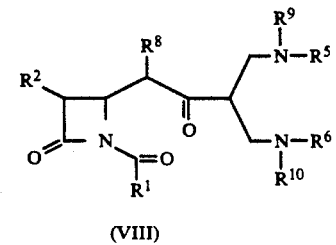

(VIII)
or salts thereof

-continued

Method C:

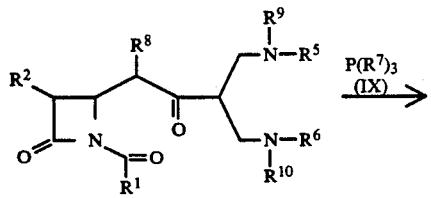

(VIII)
or salts thereof

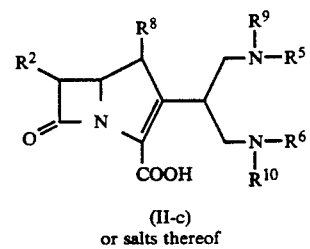

(II-c)
or salts thereof

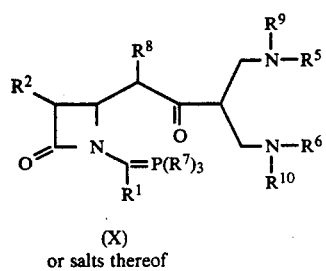 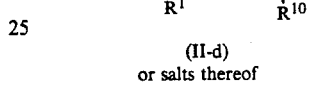

(X)
or salts thereof

Method F:

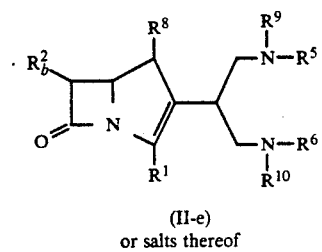

(II-d)
or salts thereof

Removal of the hydroxy-protective group on $R_a^2$ →

Method D:

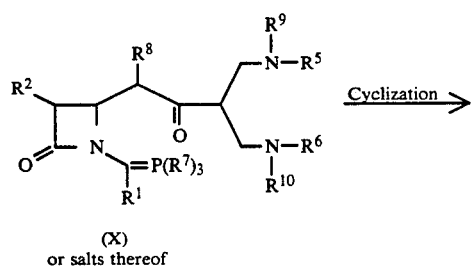

(X)
or salts thereof

Cyclization →

(II-e)
or salts thereof

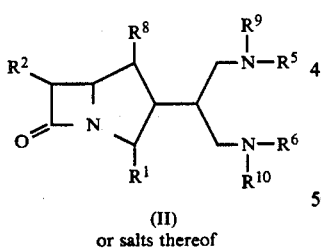

(II)
or salts thereof

Method G:

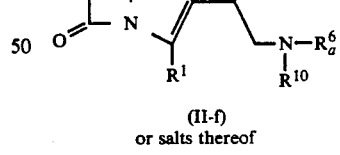

(II-f)
or salts thereof

Removal of the amino-protective group(s) on $R_a^5$ and/or $R_a^6$ →

Method E:

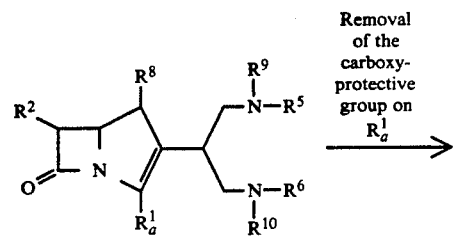

(II-b)
or salts thereof

Removal of the carboxy-protective group on $R_a^1$ →

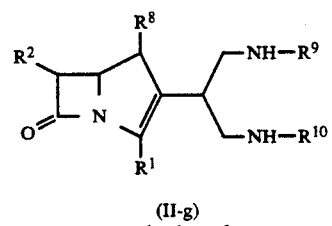

(II-g)
or salts thereof

Method H:

in which

R[1], R$_a$[1], R[2], R$_a$[2], R$_b$[2], R[3], R[4], R[8], R[9], R[10] are each as defined above, R[5] and R[6] are each hydrogen or amino-protective group, one of R$_a$[5] and R$_a$[6] is amino-protective group, and the other is hydrogen or amino-protective group, R[7] is lower alkoxy or aryl, L is a leaving group, and X is halogen.

In the above and subsequent descriptions of the present specification, suitable examples and illustrations of the various definitions which the present invention includes within the scope thereof are explained in detail as follows.

The term "lower" is intended to mean 1 to 6, preferably 1 to 4 carbon atom(s), unless otherwise indicated.

Suitable "protected carboxy" may include esterified carboxy wherein "esterified carboxy" can be referred to the ones as mentioned below.

Suitable examples of the ester moiety of an esterified carboxy may be the ones such as lower alkyl ester (e.g. methyl ester, ethyl ester, propyl ester, isopropyl ester, butyl ester, isobutyl ester t-butyl ester, pentyl ester, hexyl ester, etc.) which may have at least one suitable substituent, for example, lower alkanoyloxy(lower)alkyl ester [e.g. acetoxymethyl ester, propionyloxymethyl ester, butyryloxymethyl ester, valeryloxymethyl ester, pivaloyloxymethyl ester, hexanoyloxymethyl ester; mono(or di or tri)halo(lower)alkyl ester (e.g. 2-iodoethyl ester, 2,2,2-trichloroethyl ester, etc.); lower alkenyl ester (e.g. vinyl ester, allyl ester, etc.); ar(lower)alkyl ester which may have at least one suitable substituent (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-t-butylbenzyl ester, etc.); and the like.

More preferable example of the protected carboxy thus defined may be $C_2$–$C_4$ alkenyloxycarbonyl and phenyl(or nitrophenyl)($C_1$–$C_4$)alkoxycarbonyl and the most preferable one may be allyloxycarbonyl.

Suitable "hydroxy(lower)alkyl" may include straight or branched lower alkyl having hydroxy group such as hydroxymethyl, hydroxyethyl, hydroxypropyl, 1-(hydroxymethyl)ethyl, 1-hydroxy-1-methylethyl, hydroxybutyl, hydroxypentyl, hydroxyhexyl, and the like, in which more preferable example may be hydroxy($C_1$–$C_4$)-alkyl and the most preferable one may be 1-hydroxyethyl.

Suitable "protected hydroxy(lower)alkyl" means aforementioned hydroxy(lower)alkyl, in which the hydroxy group is protected by a conventional hydroxy-protective group such as those mentioned in the explanation of imino-protective group as mentioned below; and further ar(lower)alkyl such as mono- or di- or triphenyl(lower)alkyl (e.g. benzyl, benzhydryl, trityl, etc.), etc.; trisubstituted silyl such as tri(lower)alkylsilyl (e.g. trimethylsilyl, triethylsilyl, isopropyldimethylsilyl, t-butyldimethylsilyl, diisopropylmethylsilyl, etc.), triarylsilyl (e.g. triphenylsilyl, etc.), triar(lower)alkylsilyl (e.g. tribenzylsilyl, etc.), etc.; and the like.

More preferable example of "protected hydroxy(lower)alkyl" thus defined may be {phenyl(or nitrophenyl)($C_1$–$C_4$)alkoxy}carbonyloxy($C_1$–$C_4$)alkyl and {tri($C_1$–$C_4$)alkylsilyl}oxy($C_1$–$C_4$)alkyl, and the most preferable one may be 1-trimethylsilyloxyethyl and 1-t-butyldimethylsilyloxyethyl.

Suitable "lower alkyl" may include straight or branched one such as methyl, ethyl, propyl, isopropyl, butyl, t-butyl, pentyl, hexyl, and the like, in which more preferable example may be $C_1$–$C_4$ alkyl, and the most preferable one may be methyl.

Suitable "amino-protective group" may include acyl such as carbamoyl, aliphatic acyl, aromatic acyl, heterocyclic acyl and aliphatic acyl substituted with aromatic or heterocyclic group(s) derived from carboxylic, carbonic, sulfonic and carbamic acids.

The aliphatic acyl may include saturated or unsaturated, acyclic or cyclic ones, for example, alkanoyl such as lower alkanoyl (e.g. formyl, acetyl, propionyl, butyryl, isobutyryl, valeryl, isovaleryl, pivaloyl, hexanoyl, etc.), alkylsulfonyl such as lower alkylsulfonyl (e.g. mesyl, ethylsulfonyl, propylsulfonyl, isopropylsulfonyl, butylsulfonyl isobutylsulfonyl, pentylsulfonyl, hexylsulfonyl, etc.), carbamoyl, N-alkylcarbamoyl (e.g. methylcarbamoyl, ethylcarbamoyl, etc.), alkoxycarbonyl such as lower alkoxycarbonyl (e.g. methoxycarbonyl, ethoxycarbonyl, propoxycarbonyl, butoxycarbonyl, t-butoxycarbonyl, etc.), alkenyloxycarbonyl such as lower alkenyloxycarbonyl (e.g. vinyloxycarbonyl, allyloxycarbonyl, etc.), alkenoyl such as lower alkenoyl (e.g. acryloyl, methacryloyl, crotonoyl, etc.), cycloalkanecarbonyl such as cyclo(lower)alkanecarbonyl (e.g. cyclopropanecarbonyl, cyclopentanecarbonyl, cyclohexanecarbonyl, etc.), and the like.

The aliphatic acyl substituted with aromatic group(s) may include aralkoxycarbonyl such as phenyl(lower)alkoxycarbonyl (e.g. benzyloxycarbonyl, phenethyloxycarbonyl, etc.), and the like.

These acyl groups may be further substituted with one or more suitable substituent(s) such as nitro, aforementioned lower alkoxy and the like, and preferable acyl having such substituent(s) may be nitroaralkoxycarbonyl (e.g. nitrobenzyloxycarbonyl, etc.), lower alkoxy(lower)alkanoyl (e.g. methoxyacetyl, etc.), and the like.

More preferable example of "amino-protective group" thus defined may be $C_2$–$C_4$ alkenyloxycarbonyl and phenyl(or nitrophenyl)($C_1$–$C_4$)alkoxycarbonyl and the most preferable one may be allyloxycarbonyl and benzyloxycarbonyl.

Suitable "lower alkoxy" may include straight or branched one such as methoxy, ethoxy, propoxy, isopropoxy, butoxy, isobutoxy, pentyloxy, isopentyloxy, hexyloxy, etc., in which more preferable example may be $C_1$–$C_4$ alkoxy and the most preferable one may be methoxy for the substituent(s) in $R^3$ and ethoxy for $R^7$.

Suitable "aryl" may include $C_6$–$C_{10}$ aryl such as phenyl, tolyl, xylyl, cumenyl, mesithyl, naphthyl, and the like, in which more preferable example may be phenyl.

Suitable "leaving group" may include an inorganic acid residue such as azido, halogen (e.g. chlorine, bromine, fluorine or iodine), and the like, an organic acid residue such as acyloxy, for example, lower alkanoyloxy (e.g. acetoxy, etc.), sulfonyloxy (e.g. benzenesulfonyloxy, tosyloxy, methanesulfonyloxy, etc.), and the like, in which more preferable example may be $C_1$–$C_4$ alkanoyloxy and the most preferable one may be acetoxy.

Suitable "halogen" may include chlorine, bromine, iodine and fluorine, in which more preferable example may be chlorine.

Suitable "lower alkenyl" may include $C_2$–$C_6$ alkenyl such as vinyl, allyl, butenyl, hexenyl, etc., in which the most preferable example may be vinyl and 2-butenyl.

Suitable "mono(or di)(lower)alkylcarbamoyl" means carbamoyl which is mono(or di) substituted by aforementioned lower alkyl, wherein the most preferable example may be methylcarbamoyl and dimethylcarbamoyl.

Suitable "mono(or di)(lower)alkenylcarbamoyl" means carbamoyl which is mono(or di)substituted by aforementioned lower alkenyl, wherein more preferable example may be mono(lower)alkenylcarbamoyl, and the most preferable one may be allylcarbamoyl.

Suitable "mono(or bis)[hydroxy(lower)alkyl]carbamoyl" means carbamoyl, which is mono(or di)substituted by aforementioned hydroxy(lower)alkyl, wherein more preferable example may be mono[hydroxy(lower)alkyl]carbamoyl, and the most preferable one may be (2-hydroxyethyl)carbamoyl.

Suitable "optionally substituted cyclic-aminocarbonyl" may include cyclic-aminocarbonyl such as $C_2$–$C_7$, preferably $C_3$–$C_6$ alkyleneaminocarbonyl, which may be substituted by one or more, preferably one or two suitable substituent(s) such as lower alkyl as mentioned above, amino, nitro, hydroxy, halogen as mentioned above, etc., wherein more preferable example may be lower alkyleneaminocarbonyl optionally substituted by hydroxy, and the most preferable one may be 3-hydroxyazetidin-1-ylcarbonyl.

Suitable "acylamino" means amino group substituted by aforementioned acyl, wherein more preferable example may be lower alkanoylamino, lower alkylsulfonylamino, lower alkoxycarbonylamino and lower alkoxy(lower)alkanoylamino, and the most preferable one may be acetylamino, methoxyacetylamino, methoxycarbonylamino and methylsulfonylamino.

Suitable heterocyclic moiety of "optionally substituted heterocyclic-carbonylamino", "optionally substituted heterocyclicthio", and "optionally substituted heterocyclic group" means saturated or unsaturated, monocyclic or polycyclic heterocyclic group containing at least one hetero-atom such as an oxygen, sulfur, nitrogen atom and the like.

More preferable heterocyclic group may be heterocyclic group such as:

-unsaturated 3 to 8-membered, preferably 5 or 6-membered heteromonocyclic group containing 1 to 4 nitrogen atom(s), for example, pyrrolyl, pyrrolinyl, imidazolyl, pyrazolyl, pyridyl, and its N-oxide, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), dihydrotriazinyl (e.g., 4,5-dihydro-1,2,4-triazinyl, 2,5-dihydro-1,2,4-triazinyl, etc.), etc.;

-saturated 3 to 8-membered, preferably 5 or 6-membered heteromonocyclic group containing 1 to 4 nitrogen atom(s), for example, azetidinyl, pyrrolidinyl, imidazolidinyl, piperidinyl, pyrazolidinyl, piperazinyl, etc.;

-unsaturated condensed 7 to 12-membered heterocyclic group containing 1 to 5 nitrogen atom(s), for example, indolyl, isoindolyl, indolizinyl, benzimidazolyl, quinolyl, isoquinolyl, indazolyl, benzotriazolyl, tetrazolopyridyl, tetrazolopyridazinyl (e.g., tetrazolo[1,5-b]pyridazinyl, etc.), dihydrotriazolopyridazinyl, etc.;

-unsaturated 3 to 8-membered, preferably 5 or 6-membered heteromonocyclic group containing 1 to 2 oxygen atom(s) and 1 to 3 nitrogen atom(s), for example, oxazolyl, isoxazolyl, oxadiazolyl, (e.g., 1,2,4-oxadiazolyl, 1,3,4-oxadiazolyl, 1,2,5-oxadiazolyl, etc.), etc.;

-saturated 3 to 8-membered, preferably 5 or 6-membered heteromonocyclic group containing 1 to 2 oxygen atom(s) and 1 to 3 nitrogen atom(s), for example, morpholinyl, etc.;

-unsaturated condensed 7 to 12-membered heterocyclic group containing 1 to 2 oxygen atom(s) and 1 to 3 nitrogen atom(s), for example, benzoxazolyl, benzoxadiazolyl, etc.;

-unsaturated 3 to 8-membered, preferably 5 or 6-membered heteromonocyclic group containing 1 to 2 sulfur atom(s) and 1 to 3 nitrogen atom(s), for example, 1,3-thiazolyl, 1,2-thiazolyl, thiazolinyl, thiadiazolyl (e.g., 1,2,4-thiadiazolyl, 1,3,4-thiadiazolyl, 1,2,5-thiadiazolyl, 1,2,3-thiadiazolyl), etc.;

-saturated 3 to 8-membered, preferably 5 or 6-membered heteromonocyclic group containing 1 to 2 sulfur atom(s) and 1 to 3 nitrogen atom(s), for example thiazolidinyl, etc.;

-unsaturated 3 to 8-membered, preferably 5 or 6-membered heteromonocyclic group containing a sulfur atom, for example, thienyl, etc.;

-unsaturated condensed 7 to 12-membered heterocyclic group containing 1 to 2 sulfur atom(s) and 1 to 3 nitrogen atom(s), for example, benzothiazolyl, benzothiadiazolyl, etc. and the like;

wherein said heterocyclic group may be substituted by one or more, preferably one or two suitable substituent(s) such as:

-hydroxy;

-protected hydroxy, in which the hydroxy group is protected by a conventional hydroxy-protective group as mentioned in the explanation of protected hydroxy(lower)alkyl, more preferably $C_1$-$C_4$)alkylsilyloxy;

-hydroxy(lower)alkyl or protected hydroxy(lower)alkyl as mentioned above, more preferably hydroxy[$C_1$-$C_4$)alkyl or tri($C_1$-$C_4$)alkylsilyloxy($C_1$-$C_4$)alkyl;

-halogen;

-lower alkoxy, which may be straight or branched one such as methoxy, ethoxy, propoxy, isopropoxy, butoxy, pentyloxy, hexyloxy, etc., more preferably $C_1$-$C_4$ alkoxy;

-lower alkyl as mentioned above, more preferably $C_1$-$C_4$ alkyl (e.g. methyl, etc.);

-lower alkoxy(lower)alkyl, in which the lower alkoxy and lower alkyl moieties may respectively be the same as those for lower alkoxy and lower alkyl as mentioned above, more preferably $C_1$-$C_4$ alkoxy($C_1$-$C_4$)alkyl;

-lower alkylthio, in which the lower alkyl moiety may be the same as those for lower alkyl as mentioned above, more preferably $C_1$-$C_4$ alkylthio (e.g. methylthio, etc.); and the like.

And further when said heterocyclic group has imino-moiety(ies) in its ring, the imino-moiety(ies) may be substituted by imino-protective group, which may be the same as those for amino-protective group as mentioned above, more preferably $C_2$-$C_4$ alkenyloxycarbonyl.

Furthermore, when the heterocyclic group as stated above is, for example, imidazolyl or tetrazolyl, there are tautomeric isomers as shown by the following equilibriums:

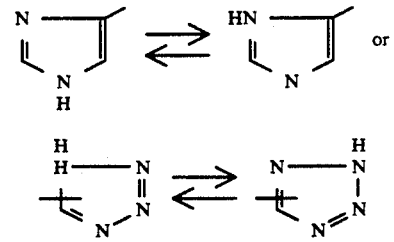

All of the above tautomeric isomers are included within the scope of the present invention and in the present invention, however, the object and intermediary compounds including the group of such tautomeric isomers are represented by using one of the expressions therefor only for the convenient sake.

Preferable heterocyclic group of "optionally substituted heterocyclic-carbonylamino" may be unsaturated 5 or 6-membered heteromonocyclic group containing 1 to 4 nitrogen atom(s) optionally substituted by lower alkylthio, in which more preferable example may be pyridyl optionally substituted by lower alkylthio.

Preferable example of "optionally substituted heterocyclic-carbonylamino" thus defined may be pyridylcarbonylamino optionally substituted by lower alkylthio and the most preferable one may be pyridin-3-ylcarbonylamino and 2-methylthiopyridin-3-ylcarbonylamino.

Preferable heterocyclic group of "optionally substituted heterocyclicthio" may be unsaturated 5 or 6-membered heteromonocyclic group containing 1 to 4 nitrogen atom(s), or containing 1 to 2 sulfur atom(s) and 1 to 3 nitrogen atom(s), each of which is optionally substituted by lower alkyl, in which more preferable example may be imidazolyl, tetrazolyl and thiadiazolyl, and each of which is oprionally substituted by lower alkyl.

Preferable example of "optionally substituted heterocyclicthio" thus defined may be imidazolylthio, tetrazolylthio and thiadiazolylthio, and each of which is optionally substituted by lower alkyl, and the most preferable one may be 1-methyltetrazol-5-ylthio, imidazol-2-ylthio, 1-methylimidazol-2-ylthio and 1,2,3-thiadiazol-5-ylthio.

Preferable "optionally substituted heterocyclic group" may be unsaturated 5 or 6-membered heteromonocyclic group containing 1 to 4 nitrogen atom(s), or containing 1 to 2 sulfur atom(s) and 1 to 3 nitrogen atom(s), each of which is optionally substituted by lower alkyl, in which more preferable example may be pyridyl, imidazolyl and thiazolyl, each of which is optionally substituted by lower alkyl.

Preferable examples of optionally substituted heterocyclic group" thus defined may be pyridyl, imidazolyl and thiazolyl, each of which is optionally substituted by lower alkyl, in which the most preferable one may be pyridin-2(or 3)-yl, 2-methylpyridin-3-yl, imidazol-1(or 2 or 4)-yl and 2-methylthiazol-4-yl.

Suitable "mono(or di)(lower)alkylcarbamoyl" moiety of "mono(or di)(lower)alkylcarbamoyloxy" may be the same as mentioned above, in which more preferable example of "mono(or di)(lower)alkylcarbamoyloxy may be mono(lower)alkylcarbamoyloxy and the most preferable one may be methylcarbamoyloxy and ethylcarbamoyloxy.

Suitable "lower alkylthio" may include straight or branched one such as methylthio, ethylthio, propylthio, isopropylthio, butylthio, t-butylthio, pentylthio, hexylthio, and the like, in which more preferable example may be $C_1$–$C_4$ alkylthio, and the most preferable one may be methylthio.

Suitable "halo(lower)alkylthio" means aforementioned lower alkylthio substituted by aforementioned halogen, in which more preferable example may be mono(or di)halo(lower)alkylthio, and the most preferable one may be difluoromethylthio.

Suitable "optionally substituted aryl" may include aforementioned aryl, which is optionally substituted by suitable group(s) as mentioned in the explanation of aforementioned heterocyclic group, in which more preferable example may be halophenyl, and the most preferable one may be 4-fluorophenyl.

Suitable "acyl" may be the same as those mentioned in the explanation of amino-protective group, in which more preferable example may be lower alkoxycarbonyl and the most preferable one may be ethoxycarbonyl.

Preferable examples of $R^3$ may be :
hydrogen;
lower alkyl (e.g. methyl, etc.);
lower alkenyl (e.g. vinyl, 2-butenyl, etc.);
lower alkoxy(lower)alkyl (e.g. methoxymethyl, etc.);
carbamoyl(lower)alkyl (e.g. carbamoylmethyl, etc.);
hydroxy(lower)alkyl (e.g. hydroxymethyl, 2-hydroxyethyl, etc.);
halo(lower)alkyl (e.g. chloromethyl, etc.);
mono(or di)(lower)alkylcarbamoyl(lower)alkyl (e.g. methylcarbamoylmethyl, dimethylcarbamoylmethyl, etc.);
mono(or di)(lower)alkenylcarbamoyl(lower)alkyl (e.g. allylcarbamoylmethyl, etc.);
mono(or bis)[hydroxy(lower)alkyl]carbamoyl(lower)alkyl [e.g. N-(2-hydroxyethyl)carbamoylmethyl, etc.];
lower alkyleneaminocarbonyl(lower)alkyl optionally substituted by hydroxy (e.g. 3-hydroxyazetidin-1-ylcarbonylmethyl, etc.);
lower alkanoylamino(lower)alkyl (e.g. acetamidomethyl, etc.);
lower alkylsulfonylamino(lower)alkyl (e.g. methylsulfonylaminomethyl, etc.);
lower alkoxycarbonylamino(lower)alkyl (e.g. methoxycarbonylaminomethyl, etc.);
lower alkoxy(lower)alkanoylamino(lower)alkyl (e.g. methoxyacetylaminomethyl, etc.);
ureido(lower)alkyl (e.g. ureidomethyl, etc.);
heterocyclic-carbonylamino(lower)alkyl, wherein the heterocyclic moiety is pyrrolyl, pyrrolinyl, imidazolyl, pyrazolyl, pyridyl, pyridyl N-oxide, pyrimidyl, pyrazinyl, pyridazinyl, triazolyl, tetrazolyl or dihydrotriazinyl and is optionally substituted by lower alkylthio (e.g. pyridin-3-ylcarbonylaminomethyl, 2-methylthiopyridin-3-ylcarbonylaminomethyl, etc.);
carbamoyloxy(lower)alkyl (e.g. carbamoyloxymethyl, etc.);
mono(or di)(lower)alkylcarbamoyloxy(lower)alkyl (e.g. methylcarbamoyloxymethyl, ethylcarbamoyloxymethyl, etc.);
lower alkylthio(lower)alkyl (e.g. methylthiomethyl, etc.);
mono or di)halo(lower)alkylthio(lower)alkyl (e.g. difluoromethylthiomethyl, etc.);
heterocyclicthio(lower)alkyl, wherein the heterocyclic moiety is pyrrolyl, pyrrolinyl, imidazolyl, pyrazolyl, pyridyl, pyridyl N-oxide, pyrimidyl, pyrazinyl, pyridazinyl, triazolyl, tetrazolyl, dihydrotriazinyl, thiazolyl, 1,2-thiazolyl, thiazolinyl or thiadiazolyl, and is optionally substituted by lower alkyl [e.g. (1-methyltetrazol-5-ylthio)methyl, imidazol-2-ylthiomethyl, (1-methylimidazol-2-ylthio)methyl, 1,2,3-thiadiazol-5-ylthiomethyl, etc.);
heterocyclic(lower)alkyl, wherein the heterocyclic moiety is pyrrolyl, pyrrolinyl, imidazolyl, pyrazolyl, pyridyl, pyridyl N-oxide, pyrimidyl, pyrazinyl, pyridazinyl, triazolyl, tetrazolyl, dihydrotriazinyl, thiazolyl, 1,2-thiazolyl, thiazolinyl or thiadiazolyl, and is optionally substituted by lower alkyl [e.g. pyridin-2(or 3)-ylmethyl, 2-methylpyridin-3-ylmethyl, imidazol-2(or 4)-ylmethyl, 3-(imidazol-1-yl)propyl, 2-methylthiazol-4-yl)ethyl, 2-(pyridin-3-yl)vinyl, etc.);
phenyl(lower)alkyl optionally substituted by halogen (e.g. 4-fluorophenylmethyl, etc.);
lower alkoxycarbonyl(lower)alkyl (e.g. ethoxycarbonylmethyl, etc.); and the like.

Preferable embodiments of $R^1$, $R^2$, $R^8$, Z, $R^3$, $R^9$ and $R^{10}$ are as follows:

$R^1$ is carboxy or protected carboxy (e.g. allyloxycarbonyl, etc.)

$R^2$ is hydroxy(lower)alkyl (e.g. 1-hydroxyethyl, etc.) or protected hydroxy(lower)alkyl [e.g. 1-(t-butyldimethylsilyloxy)ethyl, etc.], Z is a group of the formula:

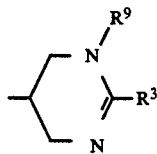

wherein
R³ is hydrogen, lower alkyl (e.g. methyl, etc.), lower alkoxy(lower)alkyl (e.g. methoxymethyl, etc.) or carbamoyl(lower)alkyl (e.g. carbamoylmethyl, etc.), and
R⁹ is hydrogen; or
R¹ is carboxy, COO⁻ or lower alkenyloxycarbonyl (e.g. allyloxycarbonyl, etc.),
R² is hydroxy(lower)alkyl (e.g. 1-hydroxyethyl, etc.) or tri(lower)alkylsilyloxy(lower)alkyl [e.g. 1-(t-butyldimethylsilyloxy)ethyl, etc.],
R⁸ is hydrogen or lower alkyl (e.g. methyl, etc.),
Z is a group of the formula:

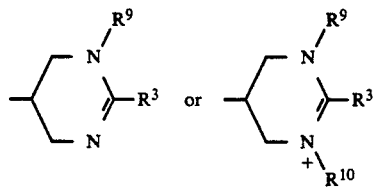

wherein
R³ is hydrogen; lower alkyl (e.g. methyl, etc.); lower alkenyl (e.g. vinyl, 2-butenyl, etc.); lower alkoxy(lower)alkyl (e.g. methoxymethyl, etc.); carbamoyl(lower)alkyl (e.g. carbamoylmethyl, etc.);
hydroxy(lower)alkyl (e.g. hydroxymethyl, 2-hydroxyethyl, etc.); halo(lower)alkyl (e.g. chloromethyl, etc.); mono(or di)(lower)alkylcarbamoyl(lower)alkyl (e.g. methylcarbamoylmethyl, dimethylcarbamoylmethyl, etc.), mono(or di)(lower)alkenylcarbamoyl(lower)alkyl(e.g. allylcarbamoylmethyl, etc.), mono(or bis)[hydroxy(lower)alkyl]carbamoyl(lower)alkyl [e.g. N-(2-hydroxyethyl)carbamoylmethyl, etc.], lower alkyleneaminocarbonyl(lower)alkyl, preferably C₃-C₆ alkyleneaminocarbonyl(lower)alkyl optionally substituted by hydroxy (e.g. 3-hydroxyazetidin-1-ylcarbonylmethyl, etc.), lower alkanoylamino(lower)alkyl (e.g. acetamidomethyl, etc.), lower alkylsulfonylamino(lower)alkyl (e.g. methylsulfonylaminomethyl, etc.), lower alkoxycarbonylamino(lower)alkyl (e.g. methoxycarbonylaminomethyl, etc.), lower alkoxy(lower)alkanoylamino(lower)alkyl (e.g. methoxyacetylaminomethyl, etc.), ureido(lower)alkyl (e.g. ureidomethyl, etc.), pyridylcarbonylamino(lower)alkyl optionally substituted by lower alkylthio (e.g. pyridin-3-ylcarbonylaminomethyl, 2-methylthiopyridin-3-ylcarbonylaminomethyl, etc.), carbamoyloxy(lower)alkyl (e.g. carbamoyloxymethyl, etc.), mono(or di)(lower)alkylcarbamoyloxy(lower)alkyl (e.g. methylcarbamoyloxymethyl, ethylcarbamoyloxymethyl, etc.), lower alkylthio(lower)alkyl (e.g. methylthiomethyl, etc.), mono(or di)halo(lower)alkylthio(lower)alkyl (e.g. difluoromethylthiomethyl, etc.), imidazolylthio(lower)alkyl, tetrazolylthio(lower)alkyl or thiadiazolylthio(-lower)alkyl, each of which is optionally substituted by lower alkyl [e.g. (1-methyltetrazol-5-ylthio)methyl, imidazol-2-ylthiomethyl, (1-methylimidazol-2-ylthio)-methyl, 1,2,3-thiadiazol-5-ylthiomethyl, etc.), pyridyl(-lower)alkyl, imidazolyl(lower)alkyl or thiazolyl(lower-)alkyl, each of which is optionally substituted by lower alkyl [e.g. pyridin-2(or 3)-ylmethyl, 2-methylpyridin-3-ylmethyl, imidazol-2(or 4)-ylmethyl, 3-(imidazol-1-yl)propyl, 2-(2-methylthiazol-4-yl)ethyl, 2-(pyridin-3-yl)vinyl, etc.), phenyl(lower)alkyl optionally substituted by halogen (e.g. 4-fluorophenylmethyl, etc.), lower alkoxycarbonyl(lower)alkyl (e.g. ethoxycarbonylmethyl, etc.),
R⁹ is hydrogen or lower alkyl (e.g. methyl, etc.), and
R¹⁰ is lower alkyl (e.g. methyl, etc.).

Suitable "ar(lower)alkyl" means aforementioned lower alkyl, which is substituted by aryl as mentioned above, in which more preferable example may be phenyl($C_1$-$C_4$)alkyl and the most preferable one may be benzyl.

The processes for the preparation of the object compound (I) of the present invention are explained in detail in the following.

(1) Process 1

The compound (I-e) or salts thereof can be prepared by reacting the compound (II-a) or salts thereof with the compound (III) or salts thereof.

Suitable salts of the compounds (I-e) and (II-a) may be the same as those for the compound (I).

Suitable salts of the compound (III) may be the same acid addition salts as those given for the compound (I).

This reaction is usually carried out in a conventional solvent which does not adversely influence the reaction such as tetrahydrofuran, dioxane, water, methanol, ethanol, buffer solution (e.g. phosphate buffer, etc.), etc., or a mixture thereof.

This reaction can be carried out in the presence of an organic or inorganic base such as those given in the explanation of Process 2.

The reaction temperature is not critical, and the reaction is usually carried out under from cooling to warming.

(2) Process 2

The compound (I-b) or salts thereof can be prepared by subjecting the compound (I-a) or salts thereof to removal reaction of the carboxy-protective group on $R_a^1$.

Suitable salts of the compounds (I-a) and (I-b) may be the same as those for the compound (I).

The present reaction is usually carried out by a conventional method such as hydrolysis, reduction, and the like.

(i) Hydrolysis

Hydrolysis is preferably carried out in the presence of a base or an acid. Suitable base may include an alkali-metal hydroxide (e.g. sodium hydroxide, potassium hydroxide, etc.), an alkaline earth metal hydroxide (e.g. magnesium hydroxide, calcium hydroxide, etc.), alkali metal hydride (e.g. sodium hydride, potassium hydride, etc.), alkaline earth metal hydride (e.g. calcium hydride, etc.), alkali metal alkoxide (e.g. sodium methoxide, sodium ethoxide, potassium t-butoxide, etc.), an alkali metal carbonate (e.g. sodium carbonate, potassium carbonate, etc.), and alkaline earth metal carbonate (e.g. magnesium carbonate, calcium carbonate, etc.), an alkali metal bicarbonate (e.g. sodium bicarbonate, potassium bicarbonate, etc.), and the like.

Suitable acid may include an organic acid (e.g. formic acid, acetic acid, propionic acid, trifluoroacetic acid, benzenesulfonic acid, p-toluenesulfonic acid, etc.) and an inorganic acid (e.g. hydrochloric acid, hydrobromic acid, sulfuric acid, phosphoric acid, etc.). The acidic hydrolysis using trifluoroacetic acid is usually accelerated by addition of cation trapping agent (e.g. phenol, anisole, etc.).

This reaction is usually carried out in a conventional solvent which does not adversely influence the reaction such as water, dichloromethane, alcohol (e.g. methanol, ethanol, etc.), tetrahydrofuran, dioxane, acetone, etc., or a mixture thereof. A liquid base or acid can be also used as the solvent.

The reaction temperature is not critical and the reaction is usually carried out under from cooling to heating.

(ii) Reduction

The reduction method applicable for this removal reaction may include, for example, reduction by using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, sulfuric acid, etc.); and conventional catalytic reduction in the presence of a conventional metallic catalyst such as palladium catalysts (e.g. spongy palladium, palladium black, palladium oxide, palladium on carbon, colloidal palladium, palladium on barium sulfate, palladium on barium carbonate, palladium hydroxide on carbon, etc.), nickel catalysts (e.g. reduced nickel, nickel oxide, Raney nickel, etc.), platinum catalysts (e.g. platinum plate, spongy platinum, platinum black, colloidal platinum, platinum oxide, platinum wire, etc.), and the like.

In case that the catalytic reduction is applied, the reaction is preferably carried out around neutral condition.

This reaction is usually carried out in a conventional solvent which does not adversely influence the reaction such as water, alcohol (e.g. methanol, ethanol, propanol, etc.), dioxane, tetrahydrofuran, acetic acid, buffer solution (e.g. phosphate buffer, acetate buffer, etc.), and the like, or a mixture thereof.

The reaction temperature is not critical and the reaction is usually carried out under from cooling to warming.

In case that the carboxy-protective group is allyl group, it can be deprotected by hydrogenolysis using a palladium compound.

Suitable palladium compound used in this reaction may be palladium on carbon, palladium hydroxide on carbon, palladium chloride, a palladium-ligand complex such as tetrakis(triphenylphosphine)palladium(0), bis(dibenzylideneacetone)palladium(0), di[1,2-bis(diphenylphosphino)ethane]palladium(0), tetrakis(triphenyl phosphite)palladium(0), tetrakis(triethyl phosphite)palladium(0), and the like.

The reaction can preferably be carried out in the presence of a scavenger of allyl group generated in situ, such as amine (e.g. morpholine, N-methylaniline, etc.), an activated methylene compound (e.g. dimedone, benzoyl acetate, 2-methyl-3-oxovaleric acid, etc.), a cyanohydrin compound (e.g. α-tetrahydropyranyloxybenzyl cyanide, etc.), lower alkanoic acid or a salt thereof (e.g. formic acid, acetic acid, ammonium formate, sodium acetate, etc.), N-hydroxysuccinimide, and the like.

This reaction can be carried out in the presence of a base such as lower alkylamine (e.g. butylamine, triethylamine, etc.), pyridine, and the like.

When palladium-ligand complex is used in this reaction, the reaction can preferably be carried out in the presence of the corresponding ligand (e.g. triphenylphosphine, triphenyl phosphite, triethyl phosphite, etc.).

This reaction is usually carried out in a conventional solvent which does not adversely influence the reaction such as water, methanol, ethanol, propanol, dioxane, tetrahydrofuran, acetonitrile, chloroform, dichloromethane, dichloroethane, ethyl acetate, etc., or a mixture thereof.

The removal reaction can be selected according to the kind of carboxy-protective group to be removed.

The present process includes within the scope thereof a case that the hydroxy-protective group on $R^2$ and/or amino-protective group(s) of $R^5$ and/or $R^6$ are removed at the same time during the reaction.

(3) Process 3

The compound (I-d) or salts thereof can be prepared by subjecting the compound (I-C) or salts thereof to removal reaction of the hydroxy-protective group on $R_a{}^2$.

Suitable salts of the compounds (I-c) and (I-d) may be the same as those for the compound (I).

This reaction is usually carried out by a conventional method such as hydrolysis, reduction and the like.

The method of hydrolysis and reduction, and the reaction conditions (e.g. reaction temperature, solvent, etc.) are substantially the same as those illustrated for removal reaction of the carboxy-protective group of the compound (I-a) in Process 2, and therefore are to be referred to said explanation.

In case that the hydroxy-protective group is tri(lower)alkylsilyl, the removal of this protective group can also be carried out in the presence of tetra(lower)alkylammonium fluoride (e.g. tetrabutylammonium fluoride, etc.).

The present process includes within the scope thereof a case that the carboxy-protective group on $R^1$ and/or amino-protective group(s) on $R^5$ and/or $R^6$ are removed at the same time during the reaction.

(4) Process 4

The compound (I-f) or salts thereof can be prepared by reacting the compound (XI) or salts thereof with the compound (III) or salts thereof.

Suitable salts of the compound (I-f) may be the same as those for the compound (I).

Suitable salts of the compound (XI) may be the same as those for the compound (II-a).

This reaction is usually carried out in a conventional solvent which does not adversely influence the reaction such as tetrahydrofuran, dioxane, water, methanol, ethanol, buffer solution (e.g. phosphate buffer, etc.), etc., or a mixture thereof.

This reaction can be carried out in the presence of an organic or inorganic base such as those given in the explanation of Process 2.

The reaction temperature is not critical, and the reaction is usually carried out under from cooling to warming.

(5) Process 5

The compound (I-e) or salts thereof can be prepared by reacting the compound (XII) or salts thereof with a base.

Suitable salts of the compound (XII) may be the same as those for the compound (XI).

This reaction is usually carried out in a conventional solvent which does not adversely influence the reaction such as tetrahydrofuran, dioxane, water, methanol, ethanol, buffer solution (e.g. phosphate buffer, etc.), etc., or a mixture thereof.

This reaction can be carried out in the presence of an organic or inorganic base such as those given in the explanation of Process 2.

The reaction temperature is not critical, and the reaction is usually carried out under from cooling to warming.

The object compound (I) obtained according to the above Processes can be isolated and purified in a conventional manner, for example, extraction, precipitation, fractional crystallization, recrystallization, chromatography, and the like.

Methods for preparing the new starting compound is explained in detail in the following.

(A) Method A

The compound (VI) or salts thereof can be prepared by reacting the compound (IV) with the compound (V) or salts thereof.

Suitable salts of the compounds (V) and (VI) may be the same acid addition salts as those for the compound (I).

The compound (V) or salts thereof can be prepared from the known compounds by a conventional manner or that described in the Preparations of the present specification.

This reaction can be carried out in the presence of a base such as alkali metal hydroxide (e.g. sodium hydroxide, potassium hydroxide, etc.), alkaline earth metal hydroxide (e.g. magnesium hydroxide, calcium hydroxide, etc.), alkali metal hydride (e.g. sodium hydride, potassium hydride, etc.), alkaline earth metal hydride (e.g. calcium hydride etc.), alkali metal alkoxide (e.g. sodium methoxide, sodium ethoxide, potassium t-butoxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), and the like.

This reaction can preferably be carried out in the presence of an enolizating agent. Suitable enolizating agent may include tri(lower)alkylsilyl trihalo(lower)alkanesulfonate, preferably tri($C_1$–$C_4$)alkylsilyl trihalo($C_1$–$C_4$)alkanesulfonate (e.g. trimethylsilyl trifluoromethanesulfonate, etc.), tin compound such as stannous (lower)alkylsulfonate which may have halogen(s), preferably stannous polyhalo($C_1$–$C_4$)alkylsulfonate (e.g. stannous trifluoromethanesulfonate, etc.), and the like.

This reaction is usually carried out in a conventional solvent which does not adversely influence the reaction such as water, dichloromethane, alcohol (e.g. methanol, ethanol, etc.), tetrahydrofuran, dioxane, acetone, etc., or a mixture thereof. A liquid base can be also used as the solvent.

The reaction temperature is not critical and the reaction is usually carried out under from cooling to warming.

(B) Method B

The compound (VIII) or salts thereof can be prepared by reacting the compound (VI) or salts thereof with the compound (VII) or salts thereof.

Suitable salts of the compound (VIII) may be the same as those for the compound (I).

Suitable salts of the compound (VII) may be salts with bases such as those given for the compound (I).

Suitable example of the compound (VII) may be oxalyl halide, in which the carboxy group may be protected by a conventional carboxy-protective group as mentioned above.

This reaction can be carried out in the presence of an inorganic or organic base such as an alkali metal bicarbonate (e.g. sodium bicarbonate, potassium bicarbonate, etc.), alkali metal carbonate (e.g. sodium carbonate, potassium carbonate, etc.), alkaline earth metal carbonate (e.g. magnesium carbonate, calcium carbonate, etc.), tri(lower)alkylamine (e.g. trimethylamine, triethylamine, N,N-diisopropyl-N-ethylamine, etc.), pyridine compounds [e.g. pyridine, picoline, lutidine, N,N-di(lower)alkylaminopyridine such as N,N-dimethylaminopyridine, etc.], quinoline, imidazole, N-lower alkylmorphorine (e.g. N-methylmorphorine, etc.), N-lower alkylpiperidine (e.g. N-ethylpiperidine, etc.), N,N-di(lower)alkylbenzylamine (e.g. N,N-dimethylbenzylamine, etc.), and the like.

This reaction is usually carried out in a conventional solvent which does not adversely influence the reaction such as dioxane, acetonitrile, chloroform, dichloromethane, hexamethylphosphoramide, dichloroethane, tetrahydrofuran, ethyl acetate, dimethyl sulfoxide, N,N-dimethylformamide, pyridine, etc., or a mixture thereof.

The reaction temperature of this reaction is not critical and the reaction is usually carried out under from cooling to warming.

(C) Method C

The compound (X) or salts thereof can be prepared by reacting the compound (VIII) or salts thereof with the compound (IX).

This reaction is usually carried out in a conventional solvent which does not adversely influence the reaction such as dioxane, acetonitrile, chloroform, dichloromethane, hexamethylphosphoramide, dichloroethane, tetrahydrofuran, ethyl acetate, dimethyl sulfoxide, N,N-dimethylformamide, pyridine, benzene, toluene, xylene, etc., or a mixture thereof.

The reaction temperature of this reaction is not critical and the reaction is usually carried out under from warming to heating.

(D) Method D

The compound (II) or salts thereof can be prepared by cyclizing the compound (X) or salts thereof.

Suitable salts of the compounds (X) and (II) may be the same as those for the compound (I).

This reaction is usually carried out in a conventional solvent which does not adversely influence the reaction such as dioxane, hexamethylphosphoramide, benzene, toluene, xylene, dimethylsulfoxide, N,N-dimethylformamide, pyridine, etc., or a mixture thereof.

The reaction temperature of this reaction is not critical and the reaction is usually carried out under from warming to heating.

(E) Method E

The compound (II-c) or salts thereof can be prepared by subjecting the compound (II-b) or salts thereof to a removal reaction of the carboxy-protective group on $R_a^1$.

Suitable salts of the compound (II-b) may be salts with acids such as those given for the compound (I).

Suitable salts of the compound (II-c) may be the same as those for the compound (II).

The present reaction is usually carried out by a conventional method such as hydrolysis, reduction, and the like.

The method of hydrolysis and reduction, and the reaction conditions (e.g. reaction temperature, solvent, etc.) are substantially the same as those illustrated for removal reaction of the carboxy-protective group of the compound (I-a) in Process 2, and therefore are to be referred to said explanation.

The present process includes within the scope thereof a case that the hydroxy-protective group on $R^2$ and/or amino-protective group(s) on $R^5$ and/or $R^6$ is removed at the same time during the reaction.

(F) Method F

The compound (II-e) or salts thereof can be prepared by subjecting the compound (II-d) or salts thereof to removal reaction of the hydroxy-protective group on $R_a{}^2$.

Suitable salts of the compounds (II-d) and (II-e) may be the same as those for the compound (II).

This reaction is usually carried out by a conventional method such as hydrolysis, reduction and the like.

The method of hydrolysis and reduction, and the reaction conditions (e.g. reaction temperature, solvent, etc.) are substantially the same as those illustrated for removal reaction of the carboxy-protective group of the compound (I-a) in Process 2, and therefore are to be referred to said explanation.

In case that the hydroxy-protective group is tri(-lower)alkylsilyl, the removal of this protective group can also be carried out in the presence of tetra(lower)alkylammonium fluoride (e.g. tetrabutylammonium fluoride, etc.).

The present process includes within the scope thereof a case that the carboxy-protective group on $R^1$ and/or amino-protective group(s) on $R^5$ and/or $R^6$ are removed at the same time during the reaction.

(G) Method G

The compound (II-g) or salts thereof can be prepared by subjecting the compound (II-f)or salts thereof to removal reaction of the amino-protective group(s) on $R_a{}^5$ and/or $R_a{}^6$.

Suitable salts of the compounds (II-f) and (II-g) may be the same as those for the compound (II).

This reaction is usually carried out by a conventional method such as hydrolysis, reduction, and the like.

The method of hydrolysis and reduction, and the reaction conditions (e.g. reaction temperature, solvent, etc.) are substantially the same as those illustrated for removal reaction of the carboxy-protective group of the compound (I-a) in Process 2, and therefore are to be referred to said explanation.

The present process includes within the scope thereof a case that the carboxy- and/or hydroxy-protective group(s) on $R^1$ and/or $R^2$ are removed at the same time during the reaction.

(H) Method H

The compound (XIV) or salts thereof can be prepared by reacting the compound (IV) with the compound (XIII) or salts thereof.

Suitable salts of the compounds (XIII) and (XIV) may be the same acid addition salts as those for the compound (I).

The compound (XIII) or salts thereof can be prepared from the known compounds by a conventional manner or that described in the Preparations of the present specification.

This reaction can be carried out in the presence of a base such as alkali metal hydroxide (e.g. sodium hydroxide, potassium hydroxide, etc.), alkaline earth metal hydroxide (e.g. magnesium hydroxide, calcium hydroxide, etc.), alkali metal hydride (e.g. sodium hydride, potassium hydride, etc.), alkaline earth metal hydride (e.g. calcium hydride etc.), alkali metal alkoxide (e.g. sodium methoxide, sodium ethoxide, potassium t-butoxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), and the like.

This reaction can preferably be carried out in the presence of an enolizating agent. Suitable enolizating agent may include tri(lower)alkylsilyl trihalo(lower)alkanesulfonate, preferably tri($C_1$-$C_4$)alkylsilyl trihalo($C_1$-$C_4$)alkanesulfonate (e.g. trimethylsilyl trifluoromethanesulfonate, etc.), tin compound such as stannous (lower)alkylsulfonate which may have halogen(s), preferably stannous polyhalo($C_1$-$C_4$)alkylsulfonate (e.g. stannous trifluoromethanesulfonate, etc.), and the like.

This reaction is usually carried out in a conventional solvent which does not adversely influence the reaction such as water, dichloromethane, alcohol (e.g. methanol, ethanol, etc.), tetrahydrofuran, dioxane, acetone, etc., or a mixture thereof. A liquid base can be also used as the solvent.

The reaction temperature is not critical and the reaction is usually carried out under from cooling to warming.

Method I

The compound (XV) or salts thereof can be prepared by subjecting the compound (XIV-a) or salts thereof to removal reaction of the amino-protective group(s) on $R_a{}^5$ and/or $R_a{}^6$.

Suitable salts of the compounds (XIV-a) and (XV) may be the same as those for the compound (XIV).

This reaction is usually carried out by a conventional method such as hydrolysis, reduction, and the like.

The method of hydrolysis and reduction, and the reaction conditions (e.g. reaction temperature, solvent, etc.) are substantially the same as those illustrated for removal reaction of the carboxy-protective group of the compound (I-a) in Process 2, and therefore are to be referred to said explanation.

The present process includes within the scope thereof a case that the carboxy- and/or hydroxy-protective group(s) on $R^1$ and/or $R^2$ are removed at the same time during the reaction.

(J) Method J

The compound (VI-a) or salts thereof can be prepared by subjecting the compound (XV) or salts thereof to a reductive cleavage reaction.

Suitable salts of the compound (VI-a) may be the same as those for the compound (VI).

The method applicable for this reaction may include, for example, reduction by using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, sulfuric acid, etc.); and conventional catalytic reduction in the presence of a conventional metallic catalyst such as palladium catalysts (e.g. spongy palladium, palladium black, palladium oxide, palladium on carbon, colloidal palladium, palladium on barium sulfate, palladium on barium carbonate, palladium hydroxide on carbon, etc.), nickel catalysts (e.g. reduced nickel, nickel oxide, Raney nickel, etc.), platinum catalysts (e.g. platinum plate, spongy platinum, platinum black, colloidal platinum, platinum oxide, platinum wire, etc.), and the like.

In case that the catalytic reduction is applied, the reaction is preferably carried out around neutral condition.

This reaction is usually carried out in a conventional solvent which does not adversely influence the reaction such as water, alcohol (e.g. methanol, ethanol, propanol, etc.), dioxane, tetrahydrofuran, acetic acid, buffer solution (e.g. phosphate buffer, acetate buffer, etc.), and the like, or a mixture thereof.

The reaction temperature is not critical and the reaction is usually carried out under from cooling to warming.

(K) Method K

The compound (VI-b) or salts thereof can be prepared by introducing an amino-protective group into the compound (VI-a) or salts thereof.

Suitable salts of the compound (VI-b) may be the same as those for the compound (VI-a).

Suitable introducing agent of the amino-protective group used in this reaction may be a conventional acylating agent which is capable of introducing the acyl group as mentioned before such as carboxylic acid, carbonic acid, sulfonic acid and their reactive derivative, for example, an acid halide, an acid anhydride, an activated amide, an activated ester, and the like. Preferable example of such reactive derivative may include acid chloride, acid bromide, a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkyl carbonate (e.g. methyl carbonate, ethyl carbonate, propyl carbonate, etc.), aliphatic carboxylic acid (e.g. pivalic acid, pentanoic acid, isopentanoic acid, 2-ethylbutyric acid, trichloroacetic acid, etc.), aromatic carboxylic acid (e.g. benzoic acid, etc.), a symmetrical acid anhydride, an activated acid amide with a heterocyclic compound containing imino function such as imidazole, 4-substituted imidazole, dimethylpyrazole, triazole and tetrazole, an activated ester (e.g. p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyridyl ester, piperidinyl ester, 8-quinolyl thioester, or an ester with a N-hydroxy compound such as N,N-dimethylhydroxylamine, 1-hydroxy-2-(1H)-pyridone, N-hydroxysuccinimide, N-hydroxyphthalimide, 1-hydroxybenzotriazole, 1-hydroxy-6-chlorobenzotriazole, etc.), and the like.

This reaction can be carried out in the presence of an organic or inorganic base such as alkali metal (e.g. lithium, sodium, potassium, etc.), alkaline earth metal (e.g. calcium, etc.), alkali metal hydride (e.g. sodium hydride, etc.), alkaline earth metal hydride (e.g. calcium hydride, etc.), alkali metal hydroxide (e.g. sodium hydroxide, potassium hydroxide, etc.), alkali metal carbonate (e.g. sodium carbonate, potassium carbonate, etc.), alkali metal bicarbonate (e.g. sodium bicarbonate, potassium bicarbonate, etc.), alkali metal alkoxide (e.g. sodium methoxide, sodium ethoxide, potassium tert-butoxide, etc.), alkali metal alkanoic acid (e.g. sodium acetate, etc.), trialkylamine (e.g. triethylamine, etc.), pyridine compound (e.g. pyridine, lutidine, picoline, 4-dimethylaminopyridine, etc.), quinoline, and the like.

In case that the introducing agent of the amino-protective group is used in a free form or its salt in this reaction, the reaction is preferably carried out in the presence of a condensing agent such as a carbodiimide compound [e.g. N,N'-dicyclohexylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.], a ketenimine compound (e.g. N,N'-carbonylbis(2-methylimidazole), pentamethyleneketene-N-cyclohexylimine, diphenylketene-N-cyclohexylimine, etc.); an olefinic or acetylenic ether compounds (e.g. ethoxyacetylene, β-chlorovinylethyl ether), a sulfonic acid ester of N-hydroxybenzotriazole derivative [e.g. 1-(4-chlorobenzenesulfonyloxy)-6-chloro-1H-benzotriazole, etc.], a combination of trialkylphosphite or triphenylphosphine and carbon tetrachloride, disulfide or diazenedicarboxylate (e.g. diethyl diazenedicarboxylate, etc.), a phosphorus compound (e.g. ethyl polyphosphate, isopropyl polyphosphate, phosphoryl chloride, phosphorus trichloride, etc.), thionyl chloride, oxalyl chloride, N-ethylbenzisoxazolium salt, N-ethyl-5-phenylisoxazolium-3-sulfonate, a reagent (referred to a so-called "Vilsmeier reagent") formed by the reaction of an amide compound such as N,N-di(lower)alkylformamide (e.g. dimethylformamide, etc.), N-methylformamide or the like with a halogen compound such as thionyl chloride, phosphoryl chloride, phosgene or the like.

The reaction is usually carried out in a conventional solvent which does not adversely influence the reaction such as water, acetone, dichloromethane, alcohol (e.g. methanol, ethanol, etc.), tetrahydrofuran, pyridine, N,N-dimethylformamide, etc., or a mixture thereof, and further in case that the imino-introducing agent is in liquid, it can also be used as a solvent.

The reaction temperature is not critical and the reaction is usually carried out under from cooling to heating.

(L) Method L

The compound (XII) or salts thereof can be prepared by reacting the compound (II-a) or salts thereof with the compound (III) or salts thereof.

This reaction is usually carried out in a conventional solvent which does not adversely influence the reaction such as tetrahydrofuran, dioxane, water, methanol, ethanol, buffer solution (e.g. phosphate buffer, etc.), etc., or a mixture thereof.

This reaction can be carried out in the presence of an organic or inorganic base such as those given in the explanation of Process 2.

The reaction temperature is not critical, and the reaction is usually carried out under from cooling to warming.

(M) Method M

The compound (III) or salts thereof can be prepared by reacting the compound (XVI) or salts thereof with the compound (XVII).

Suitable salts of the compound (XVI) may be the same acid addition salts as those given for the compound (I).

This reaction is usually carried out in a conventional solvent which does not adversely influence the reaction such as tetrahydrofuran, dioxane, water, methanol, ethanol, buffer solution (e.g. phosphate buffer, etc.), etc., or a mixture thereof.

This reaction can be carried out in the presence of an organic or inorganic acid such as those given in the explanation of Process 2.

The reaction temperature is not critical, and the reaction is usually carried out under from cooling to warming.

The object compound (I) and pharmaceutically acceptable salts thereof of the present invention are novel and exhibit high antimicrobial activity, inhibiting the growth of a wide variety of pathogenic microorganisms including Gram-positive and Gram-negative microorganisms and are useful as antimicrobial agents.

Now in order to show the utility of the object compound (I), the test data on antimicrobial activity of the representative compound of the compound (I) of this invention is shown in the following.

In Vitro Antimicrobial Activity

Test Method

In vitro Antimicrobial Activity was determined by the two-fold agar-plate dilution method as described below.

One loopful of an overnight culture of a test strain in Trypticase-soy broth ($10^6$ viable cells per ml) was streaked on heart infusion agar (HI-agar) containing graded concentrations of the test compound, and the minimal inhibitory concentration (MIC) was expressed in terms of $\mu g/ml$ after incubation at 37° C. for 20 hours.

Test Compound

The compound of Example 1.

Test Result

| Test Strain | MIC ($\mu g/ml$) |
|---|---|
| S. aureus 6 | ≦0.025 |

For therapeutic administration, the object compound (I) and the pharmaceutically acceptable salts thereof of the present invention are used in the form of conventional pharmaceutical preparation which contains said compound, as an active ingredient, in admixture with pharmaceutically acceptable carriers such as an organic or inorganic solid or liquid excipient which is suitable for oral, parenteral and external administration. The pharmaceutical preparations may be in solid form such as tablet, granule, powder, capsule, or liquid form such as solution, suspension, syrup, emulsion, lemonade, and the like.

If needed, there may be included in the above preparations auxiliary substances, stabilizing agents, wetting agents and other commonly used additives such as lactose, stearic acid, magnesium stearate, terra alba, sucrose, corn starch, talc, gelatin, agar, pectin, peanut oil, olive oil, cacao butter, ethylene glycol, tartaric acid, citric acid, fumaric acid, and the like.

While the dosage of the compound (I) may vary from and also depend upon the age, conditions of the patient, a kind of diseases, a kind of the compound (I) to be applied, etc. In general, amount between 1 mg and about 4,000 mg or even more per day may be administered to a patient. An average single dose of about 1 mg, 10 mg, 50 mg, 100 mg, 250 mg, 500 mg, 1000 mg, 2000 mg, of the object compound (I) of the present invention may be used in treating diseases infected by pathogenic microorganisms.

The following Preparations and Examples are given for the purpose of illustrating this invention in more detail.

Preparation 1

To a solution of 70.2 g of ethyl 2-(N-benzylaminomethyl)-3-t-butyldimethylsilyloxybutanoate in methanol (100 ml) was added portionwise 10.0 g of 10% wet palladium on carbon under nitrogen atmosphere. The mixture was shaken vigorously under 3.5 atmospheric pressure of hydrogen. After 8 hours, palladium on carbon was filtered off and washed with chloroform. The filtrate was evaporated to dryness under reduced pressure to give 50.3 g of crude ethyl 2-aminomethyl-3-t-butyldimethylsilyloxybutanoate.

IR (Neat): 2940, 1725, 1460, 1375, 1252, 1095, 834, 774 cm$^{-1}$.

NMR (CDCl$_3$, δ): 0.06–0.10 (6 H, m), 0.87 (9 H, s), 1.15
(3 H, d, J=7.7 Hz), 1.28 (3 H, t, J=7.1 Hz), 1.66
(2 H, br), 2.36–2.48 (1 H, m), 2.94–3.05 (2 H, m),
4.05–4.22 (3 H, m).

Preparation 2

To a suspension of 17.4 g of lithium aluminum hydride in 400 ml of tetrahydrofuran was added a solution of 50.6 g of ethyl 2-aminomethyl-3-t-butyldimethylsilyoloxybutanoate in 100 ml of tetrahydrofuran dropwise at −50° C. under nitrogen. The mixture was stirred vigorously below 0° C. for 6 hours. The mixture was quenched carefully with 41 ml of saturated aqueous sodium sulfate solution at −30° C. and the solution was stirred overnight. White solid was filtered off and washed with tetrahydrofuran. The filtrate was evaporated under reduced pressure to give 2-aminomethyl-3-tbutyldimethylsilyloxybutan-1-ol. To the residue were added 420 ml of tetrahydrofuran and 400 ml of water. Under ice bath cooling, 21.4 ml of allyl chloroformate was added dropwise to the solution, while the pH was kept constant at 8.0–8.5 by dropping 4N sodium hydroxide solution. After dropping, the reaction mixture was stirred until the pH became unchanged. The reaction mixture was extracted with ethyl acetate, and the organic layer was washed with saturated aqueous sodium hydrogen carbonate solution and brine, dried over anhydrous sodium sulfate, and evaporated under reduced pressure to give 40.8 g of 2-(N-allyloxycarbonylaminomethyl)-3-t-butyldimethylsilyloxybutan-1-ol.

IR (Neat): 3350, 2950, 1720, 1700, 1520, 1510, 1250, 834, 773 cm$^{-1}$.

NMR (CDCl$_3$, δ): 0.07 (3 H, s), 0.08 (3 H, s), 0.89 (9 H,
s), 1.22 (3 H, d, J=6.4 Hz), 1.65 (1 H, br), 2.96

(1 H, br), 3.24–3.50 (2 H, m), 3.65 (2 H, br t), 3.99 (1 H, m), 4.56 (2 H, d, J=5.4 Hz), 5.18–5.34 (3 H, m), 5.84–5.98 (1 H, m).

Preparation 3

To a solution of 7.00 g of 2-(N-allyloxycarbonylaminomethyl)-3-t-butyldimethylsilyloxybutan-1-ol and 4.60 ml of triethylamine in 35 ml of dichloromethane was added dropwise 2.05 ml of methanesulfonyl chloride at −10° C. After stirring for 3 hours, water was added to the reaction mixture and then the solution was extracted with chloroform. The organic layer was washed in turn with 1N hydrochloric acid and brine, and dried over anhydrous magnesium sulfate. Evaporation of the solvent followed by a column chromatography on silica gel (hexane:ethyl acetate=3:1) gave 8.8 g of 2-(N-allyloxycarbonylaminomethyl)-3-t-butyldimethylsilyloxy-1-methanesulfonyloxybutane.

NMR (CDCl$_3$, δ): 0.09 (6 H, s), 0.90 (9 H, s), 1.24 (3 H, d, J=6.4 Hz), 1.90–1.97 (1 H, br), 3.02 (3 H, s), 3.24–3.36 (1 H, m), 3.51–3.64 (1 H, m), 4.07–4.14 (1H, m), 4.29 (2 H, d, J=6.8 Hz), 4.55 (2 H, br d, J=5.4 Hz), 5.17–5.33 (2 H, m), 5.45 (1 H, br), 5.81–5.97 (1 H, m).

Preparation 4

To a solution of 7.00 g of 2-(N-allyloxycarbonylaminomethyl)-3-t-butyldimethylsilyloxy-1-methanesulfonyloxybutane and 1.42 g of ammonium chloride in 70 ml of N,N-dimethylformamide was added 1.73 g of sodium azide at 0° C. The mixture was stirred at 50° C. for 7 hours. After the starting material disappeared, 350 ml of ethyl acetate and 350 ml of water were added to the reaction mixture. The organic layer was washed in turn with water three times and brine. The half amount of solvent was evaporated and then 5.11 g of triphenylphosphine was added thereto portionwise. After stirring overnight, 2.15 g of 28% aqueous ammonia was added and the mixture was stirred for 8 hours, and then evaporated under reduced pressure to give 11.36 g of crude 2-(N-allyloxycarbonylaminomethyl)-3-(t-butyldimethylsilyloxy)butylamine.

NMR (CDCl$_3$, δ): 0.07 (6 H, m), 0.90 (9 H, s), 1.21 (3 H, d, J=6.4 Hz), 1.46 (1 H, m), 1.74 (2 H, br), 2.78 (2 H, d, J=6.2 Hz), 3.24–3.60 (2 H, m), 3.97–4.02 (1 H, m), 4.55 (2 H, d, J=5.4 Hz), 5.16–5.33 (2 H, m), 5.84–5.98 (2 H, m).

Preparation 5

To a solution of 11.4 g of crude 2-(N-allyloxycarbonylaminomethyl)-3-(t-butyldimethylsilyloxy)butylamine in 67 ml of tetrahydrofuran and 56 ml of water was added 2.8 ml of allyl chloroformate dropwise, while keeping pH 8–8.5 with 4N sodium hydroxide solution. The reaction mixture was extracted three times with chloroform, and the combined organic layer was washed with brine and dried over anhydrous magnesium sulfate. Evaporation of the solvent followed by column chromatography on silica gel (hexane:ethyl acetate=1:1) gave 5.34 g of 1-allyloxycarbonylamino-2-(N-allyloxycarbonylaminomethyl)- 3-t-butyldimethylsilyloxybutane.

IR (Neat): 3325, 2940, 1720, 1705, 1525, 1510, 1250, 835, 776 cm$^{-1}$.

NMR (CDCl$_3$, δ): 0.07 (3 H, s), 0.08 (3H, s), 0.90 (9 H, s), 1.22 (3 H, d, J=6.2 Hz), 1.70 (1 H, br), 3.02–3.51 (4 H, m), 3.94–3.99 (1 H, m), 4.55 (4 H, d, J=5.5 Hz), 5.17–5.35 (4 H, m), 5.40 (1 H, br), 5.57 (1 H, br), 5.80–5.98 (2 H, m).

Preparation 6

To a solution of 3.98 g of 1-allyloxycarbonylamino-2-(N-allyloxycarbonylaminomethyl)-3-t-butyldimethylsilyloxybutane in 20 ml of acetonitrile was added 2 ml of concentrated hydrochloric acid at 0° C. After stirring for 3 hours at room temperature, the mixture was extracted with chloroform and the organic layer was washed with saturated sodium hydrogen carbonate and brine, and dried over anhydrous magnesium sulfate. Evaporation of the solvent followed by a column chromatography on silica gel (hexane:ethyl acetate=1:1) gave 2.88 g of 1-allyloxycarbonylamino-2-(N-allyloxycarbonylaminomethyl)butan-3-ol quantitatively.

IR (Neat): 3315, 2950, 1716, 1700, 1690, 1540, 1520, 1255, 1138, 990, 925, 774 cm$^{-1}$.

NMR (CDCl$_3$, δ): 1.26 (3 H, d, J=6.3 Hz), 1.52 (1 H, br), 3.05–3.24 (3 H, m), 3.51–3.78 (2 H, m), 4.56 (4 H, d, J=4.3 Hz), 5.19–5.35 (5 H, m), 5.82–6.02 (3 H, m).

Preparation 7

To a solution of 0.32 ml of oxalyl chloride in 10 ml of dichloromethane was added 0.54 ml of dimethyl sulfoxide at −78° C. under nitrogen. After stirring for 5 minutes, a solution of 1.00 g of 1-allyloxycarbonylamino-2-(N-allyloxycarbonylaminomethyl)butan-3-ol in 2 ml of dichloromethane was added. After stirring for 30 minutes, 2.43 ml of triethylamine was added to the mixture and then the temperature of the mixture was raised to room temperature. The mixture was extracted with chloroform and the organic layer was washed in turn with 1N hydrochloric acid, saturated aqueous sodium hydrogen carbonate solution and brine, and dried over anhydrous magnesium sulfate. Evaporation of the solvent followed by a column chromatography on silica gel (hexane:ethyl acetate=1:1) gave 0.77 g of 1-allyloxycarbonylamino-2-(N-allyloxycarbonylaminomethyl)-butan-3-one.

IR (CHCl$_3$): 3440, 2935, 1706, 1510, 1250, 1145, 990, 933 cm$^{-1}$.

NMR (CDCl$_3$, δ): 2.25 (3 H, s), 2.87 (1 H, m), 3.27 (2 H, m), 3.61 (2 H, m), 4.55 (4 H, d, J=5.6 Hz), 5.22 (2 H, d, J=12.4 Hz), 5.29 (2 H, d, J=17.3 Hz), 5.52 (2 H, br), 5.91 (2 H, m).

Preparation 8

To a solution of 500 mg of 1-allyloxycarbonylamino-2-(N-allyloxycarbonylaminomethyl)butan-3-one and 0.96 ml of 1 -ethylpiperidine in 4 ml of dichloromethane was added 1.12 ml of trimethylsilyl trifluoromethanesulfonate at −20° C. The mixture was stirred at room temperature for 3 hours (solution A). To a solution of 0.81 g of (3R,4R)-4-acetoxy-3-[(R)-1-(t-butyldimethylsilyloxy)ethyl]-2-azetidinone and 0.39 ml of 1-ethylpiperidine in 4 ml of dichloromethane was added 0.55 ml of trimethylsilyl trifluoromethanesulfonate at −50° C. the mixture was stirred at 0° C. for 2 hours (solution B). A solution of solution B and 0.20 ml of trimethylsilyl trifluoromethanesulfonate were added sequentially to the solution A at −50° C. The mixture was stirred for 2 hours at 0° C. 10 ml of Water and 14 ml of ethyl acetate were added thereto. The mixture was stirred for 20 minutes at 0° C., extracted with ethyl acetate three times. The organic layer was washed with 1N hydrochloric acid solution, saturated aqueous sodium hydrogen carbonate and brine, and evaporated under reduced pressure. The residue was chromatographed on silica gel to give 0.38 g of (3S,4R)-4-[4-allyloxycarbonylamino-3-(N-allyloxycarbonylaminomethyl)-2-oxobutyl]-3-[(R)-1-(t-butyldimethylsilyloxy)ethyl]-2-oxoazetizine.

IR (CHCl$_3$): 3400, 2950, 1755, 1740, 1728, 1710, 1510, 1372, 1260, 1142, 1091, 1043, 989, 938, 834 cm$^{-1}$.

NMR (CDCl$_3$, $\delta$): 0.03 (6 H, s), 0,82 (9 H, s), 1.15 (3 H, d, J=5.4 Hz), 2.67–2.90 (4 H, m), 3.30–3.43 (4 H, br), 3.90 (1H, m), 4.12 (1H, m), 4.46 (4 H, d, J=5.4 Hz), 5.06–5.30 (4 H, m), 5.45–6.05 (4 H, m), 6.42 (1H, br s).

Preparation 9

To a solution of 1.98 g of (3S,4R)-4-[4-allyloxycarbonylamino-3-(N-allyloxycarbonylaminomethyl)-2-oxobutyl]-3-[(R)-1-(t-butyldimethylsilyloxy)ethyl]-2-oxoazetidine and 0.92 ml of triethylamine in 20 ml of dichloromethane was added 0.72 ml of allyl oxalyl chloride dropwise at −60° C. After stirring for 1 hour, the reaction mixture was quenched with water, extracted three times with dichloromethane. The extract was washed with 1N hydrochloric acid solution, saturated sodium hydrogen carbonate solution and brine, successively, dried over anhydrous magnesium sulfate, and evaporated under reduced pressure. The residue was purified by a column chromatography on silica gel to give 2.29 g of allyl 2-[(3S,4R)-4-[4-allyloxycarbonylamino-3-(N-allyloxycarbonylaminomethyl)-2-oxobutyl]-3-[(R)-1-(t-butyldimethylsilyloxy)ethyl]-2-oxoazetidin-1-yl]-2-oxoacetate.

IR (CHCl$_3$): 3430, 2950, 1806, 1750, 1720, 1710, 1510, 1387, 1371, 1250, 836 cm$^{-1}$.

Preparation 10

A solution of 0.48 g of allyl 2-[(3S,4R)-4-(4-allyloxycarbonylamino-3-(N-allyloxycarbonylaminomethyl)-2-oxobutyl]-3-[(R)-1-(t-butyldimethylsilyloxy)ethyl]-2-oxoazetidin-1-yl]-2-oxoacetate and 0.39 ml of triethyl phosphite in 2.4 ml of toluene was stirred at 90° C. for 10 hours. After ylid was identified by thin layer chromatography the temperature was raised to 130° C. and 42 mg of hydroquinone was added. After stirring for 4 hours at 130° C., the reaction mixture was cooled to room temperature and then ethyl acetate was added. The organic layer was washed in turn with 5% aqueous potassium carbonate and brine, dried over anhydrous magnesium sulfate and evaporated under reduced pressure. The residue was chromatographed on silica gel to give 0.28 g of allyl (5R,6S)-3-[2-allyloxycarbonylamino-1-(N-allyloxycarbonylaminomethyl)ethyl]-6-[(R)-1-(t-butyldimethylsilyloxy)ethyl]-7-oxo-1-azabicyclo[3.2.0]hept-2-ene-2-carboxylate.

IR (CHCl$_3$): 3430, 2950, 1774, 1720, 1510, 1371, 1250, 1042, 833 cm$^{-1}$.

Preparation 11

To a solution of 1.74 g of allyl (5R,6S)-3-[2-allyloxycarbonylamino-1-(N-allyloxycarbonylaminomethyl)ethyl]-6-[(R)-1-(t-butyldimethylsilyloxy)ethyl]-7-oxo-1-azabicyclo[3.2.0]hept-2-ene-2-carboxylate and 0.54 ml of acetic acid in 9 ml of tetrahydrofuran was added dropwise 3.29 g of 70 % tetrabutylammonium fluoride at room temperature. The mixture was stirred for 20 hours at room temperature. 60 ml of Ethyl acetate and 45 ml of water were added to the reaction mixture and the aqueous layer was extracted three times with ethyl acetate. The extracts were combined, washed in turn with saturated aqueous sodium hydrogen carbonate and brine, dried over anhydrous magnesium sulfate and evaporated. The residue was chromatographed on silica gel to give 766 mg of allyl (5R,6S)-3-[2-allyloxycarbonylamino-1-(N-allyloxycarbonylaminomethyl)ethyl]-6-[(R)-1-hydroxyethyl]-7-oxo-1-azabicyclo[3.2.0]hept-2-ene-2-carboxylate.

IR (CHCl$_3$) 3430, 2965, 1774, 1718, 1510, 1371, 1326, 1245, 1100, 1041, 990, 933 cm$^{-1}$.

Preparation 12-1)

A mixture of 4-chloromethyl-1-tritylimidazole hydrochloride (35 g), water (600 ml), ethyl acetate (300 ml), tetrahydrofuran (250 ml) was adjusted to pH 9.5 with 30% aqueous potassium carbonate. The organic layer was separated, washed with brine and evaporated. The residue was taken up into dimethyl sulfoxide (250 ml) and to the solution was added sodium cyanide (13.01 g). The mixture was heated to 70° C. for 4 hours and diluted with a mixture of ethyl acetate (1 l) and water (1 l). The organic layer was separated, washed with water (200 ml×4) and brine, dried over magnesium sulfate and evaporated. The residue was triturated with diisopropyl ether to give 4-cyanomethyl-1-tritylimidazole (27.1 g).

IR (Nujol): 2250 cm$^{-1}$.

NMR (CDCl$_3$, $\delta$): 3.68 (2 H, s), 6.78–7.45 (17 H, m).

Preparation 12-2)

4-Cyanomethyl-1-tritylimidazole (27.0 g) was dissolved in trifluoroacetic acid (70 ml). After stirring for 1 hour, to the mixture was added ethanol (60 ml) and the mixture was evaporated. The resulting precipitate was filtered off, and the filtrate was evaporated. The residue was taken up into a mixture of ethanol (5 ml) and chloroform (30 ml) and into the mixture was absorbed hydrogen chloride gas (6.2 g) at 0° C. The resulting mixture was allowed to stand at 5° C. overnight and evaporated. The residue was triturated with diisopropyl ether to give ethyl 2-(imidazol-4-yl)acetimidate dihydrochloride.

NMR (DMSO—d$_6$, $\delta$) : 1.40 (3 H, t, J=7 Hz), 4.34 (2 H, s), 4.50 (2 H, q, J=7 Hz), 7.0–8.0 (1H, m), 9.0–9.2 (1H, m).

Preparation 13-1)

A mixture of 4-bromobutyronitrile (5.6 g) and 1-methylimidazole (3.0 ml) in benzene (20 ml) was heated to 60° C. for 6 hours. The resulting syrup was separated by decantation, washed with ether and dried to give 4-(3-methyl-1-imidazolio)butyronitrile bromide (7.43 g).

NMR (DMSO—d$_6$, $\delta$) : 2.07–2.25 (2 H, m), 2.62 (2 H, t, J=7 Hz), 3.87 (3 H, s), 4.28 (2 H, t, J=7 Hz), 7.75–7.95 (2 H, m), 9.28 (1H, s).

Preparation 13-2)

Ethyl 4-(3-methylimidazolio)butanimidate bromide hydrochloride was obtained in substantially the same method as that of Preparation 14-3).

NMR (DMSO—d$_6$, $\delta$) : 1.36 (3 H, t, J=7 Hz), 2.01–2.25 (2 H, m), 2.60–2.80 (2 H, m), 3.88 (3 H, s), 4.20–4.40 (2 H, m), 4.45 (2 H, q, J=7 Hz), 7.70–7.90

(2 H, m), 9.30–9.40 (1 H, m).

Preparation 14-1)

2-Cyanomethyl-1-tritylimidazole was obtained in 87.9% yield in substantially the same manner as that of Preparation 12-1).

NMR (DMSO—$d_6$, δ) : 3.15 (2 H, s), 6.74–7.52 (17 H, m).

Preparation 14-2)

2-Cyanomethyl-1-tritylimidazole (25 g) was dissolved in trifluoroacetic acid (70 ml). After stirring for 3 hours, to the reaction mixture was added ethanol (70 ml) and the solvent was removed in vacuo. Resulting solid was collected and washed with diisopropyl ether to give 2-cyanomethylimidazole trifluoroacetate (12.67 g).

NMR (DMSO—$d_6$, δ) : 4.58 (2 H, s), 7.59 (2 H, s).

Preparation 14-3)

Into the suspension of 2-cyanomethylimidazole trifluoroacetate (7 g) in a mixture of chloroform (25 ml) and ethanol (2.42 ml) was absorbed hydrogen chloride gas (2.54 g) at 0° C. The resulting mixture was allowed to stand at 0° C. for 7 days. The residue was triturated with diisopropyl ether to give ethyl 2-(imidazol-2-yl)acetimidate dihydrochloride (6.28 g).

NMR (DMSO—$d_6$, δ): 1.23 (3 H, t, J=7.11 Hz), 4.18 (2 H, q, J=7.11 Hz), 4.46 (2 H, s), 7.65–7.73 (2 H, m).

Preparation 15

Ethyl 2-(pyridin-2-yl)acetimidate dihydrochloride was obtained in substantially the same manner as that of Preparation 14-3).

NMR (DMSO—$d_6$, δ): 1.41 (3 H, t, J=7 Hz), 4.48 (2 H, s), 4.56 (2 H, q, J=7 Hz), 7.90–9.00 (4 H, m).

Preparation 16-1)

To a suspension of lithium aluminum hydride (6.2 g) in tetrahydrofuran (400 ml) was added dropwise ethyl 2-methylnicotinate (25 g) at −20° C. After stirring for 1 hour, to the reaction mixture was added dropwise in turn water (6.2 ml), 4N-aqueous sodium hydroxide (6.2 ml) and water (18.6 ml). The precipitate was filtered off and the filtrate was concentrated in vacuo to give 3-hydroxymethyl-2-methylpyridine (16.2 g).

NMR (CDCl$_3$, δ): 2.45 (3 H, s), 4.68 (2 H, s),
7.08–7.14 (1H, m), 7.72–7.76 (1H, m), 8.23–8.27 (1 H, m).

Preparation 16-2)

To a solution of 3-hydroxymethyl-2-methylpyridine (10.42 g) in toluene (100 ml) was added dropwise thionyl chloride (9.87 ml) at 25° C. After 2.5 hours, the solvent was removed in vacuo to give a residual solid. The solid was dissolved in 4N-aqueous sodium hydroxide (100 ml) and extracted with ethyl acetate. The organic layer was separated, washed with brine and dried over magnesium sulfate. Concentration of the solution gave 3-chloromethyl-2-methylpyridine (9.22 g).

NMR (DMSO—$d_6$, δ): 2.56 (3 H, s), 4.83 (2 H, s),
7.21–7 27 (1H, m), 7.76–7.81 (1H, m),
8.40–8.44 (1H, m).

Preparation 16-3)

The mixture of 3-chloromethyl-2-methylpyridine (9.2 g) and sodium cyanide (9.55 g) in dimethyl sulfoxide (80 ml) was stirred for 30 minutes at 80° C. The reaction mixture was poured into a mixture of water (200 ml) and ethyl acetate (1 l). Organic layer was separated, washed with brine and dried over magnesium sulfate. Concentration of the solvent gave a residue, which was chromatographed on silica gel (300 ml) eluting with a mixture of hexane and ethyl acetate (1:4, V/V) to give 3-cyanomethyl-2-methylpyridine (7.6 g).

NMR (DMSO—$d_6$, δ): 2.49 (3 H, s), 4.07 (2 H, s),
7.24–7.30 (1 H, m), 7.68–7.74 (1H, m),
8.40–8.43 (1 H, m).

Preparation 16-4)

Ethyl 2-(2-methylpyridin-3-yl)acetimidate dihydrochloride was obtained in substantially the same manner as that of Preparation 14-3).

NMR (DMSO—$d_6$, δ): 1.41 (3 H, t, J=7 Hz), 2.76 (3 H, s),
4.46 (2 H, s), 4.49 (2 H, q, J=7 Hz), 7.86–8.78 (3 H, m).

Preparation 17-1)

To a suspension of sodium hydride (62% oil, 10.87 g) in tetrahydrofuran (200 ml) was added successively diethyl cyanomethylphosphonate (43.25 ml) and pyridine-3-carbaldehyde (24 ml) at 0° C. Then, the reaction mixture was heated to refluxing temperature. After 5 hours the reaction mixture was poured into a mixture of ethyl acetate (1 l) and water (200 ml). The organic layer was separated, washed with brine and dried over magnesium sulfate. Evaporation of the solvent gave a residue, which was chromatographed on silica gel (600 ml) eluting with ethyl acetate to give 3-(3-pyridyl)acrylonitrile (23.9 g).

NMR (DMSO—$d_6$, δ): 6.64 (1H, d, J=16.8 Hz),
7.12–7.53 (1H, m), 7.73 (1H, d, J=16.8 Hz),
8.07–8.15 (1H, m), 8.62–8.66 (1H, m),
8.82–8.83 (1H, m).

Preparation 17-2)

To a suspension of 3-(3-pyridyl)acrylonitrile (11 g) and 20% palladium on carbon (50% wet 2.5 g) in methanol was stirred for 4 hours at 25° C. under hydrogen atmosphere. The catalyst was filtered off and the filtrate was evaporated in vacuo to give 3-pyridylpropiononitrile (11.3 g).

NMR (DMSO—$d_6$, δ): 2.80–2.95 (4 H, m), 7.30–7.40 (1H,
m), 7.70–7.77 (1H, m), 8.46–8.54 (2 H, m).

Preparation 18-1)

Ethyl 3-(3-pyridyl)propionimidate dihydrochloride was obtained in substantially the same manner as that of Preparation 14-3).

NMR (DMSO—$d_6$, δ): 1.29 (3 H, t, J=7 Hz), 3.00–3.10
(4 H, m), 4.45 (2 H, q, J=7 Hz), 8.00–8.14 (1H, m)

Preparation 18-2)

Ethyl 3-(3-pyridyl)acrylimidate dihydrochloride was obtained in substantially the same manner as that of Preparation 14-3).

NMR (DMSO—$d_6$, δ) : 1.47 (3 H, t, J=7 Hz), 4.64 (2 H, q,
J=7 Hz), 7.04 (1H, d, J=16.8 Hz), 7.90 (1H, d,
J=16.8 Hz), 8.10–8.22 (1H, m), 8.77–9.28 (3 H, m).

Preparation 19-1)

To a stirred solution of aminoacetonitrile hydrochloride (5.95 g) in a mixture of water (100 ml) and tetrahydrofuran (100 ml) was added slowly 2 -(methylthio)-nicotinoyl chloride (10 g) at 0° C. while adjusting pH to 8-9 with 4N-aqueous sodium hydroxide. After stirring for 30 minutes at 0° C., the solvent was evaporated to give a residue, which was chromatographed on silica gel (350 ml) eluting with ethyl acetate to give [2-(methylthio)nicotinoyl]aminoacetonitrile (9.9 g).

NMR (DMSO—$d_6$, $\delta$): 2.45 (3 H, s), 4.33 (2 H, d, J=5.48 Hz), 7.19-7.25 (1H, m), 7.83-7.88 (1H, m), 8.57-8.60 (1H, m), 9.22-9.28 (1H, m).

Preparation 19-2)

Ethyl [2-(methylthio)nicotinoyl]aminoacetimidate dihydrochloride was obtained in substantially the same manner at that of Preparation 14-3).

NMR (DMSO—$d_6$, $\delta$) : 1.41 (3 H, t, J=7 Hz), 4.31 (2 H, s),
4.53 (2 H, q, J=7 Hz), 7.20-9.20 (4 H, m).

Preparation 20-1)

(Nicotinoylamino)acetonitrile was obtained in substantially the same manner as that of Preparation 19-1).

NMR (DMSO—$d_6$, $\delta$): 4.39 (2 H, s), 7.53-7.60 (1H, m),
8.21-8.27 (1H, m), 8.76-8.79 (1H, m), 9.04-9.06 (1H, m), 9.46 (1H, br s).

Preparation 20-2)

Ethyl nicotinoylaminoacetimidate dihydrochloride was obtained in substantially the same manner as that of Preparation 14-3).

NMR (DMSO—$d_6$, $\delta$) : 1.37 (3 H, t, J=7 Hz), 4.42 (2 H, s),
4.55 (2 H, q, J=7 Hz), 8.20-10.00 (5 H, m).

Preparation 21-1)

To a stirred solution of sodium 1,2,3-thiadiazol-5-thiolate (15 g) in dichloromethane (150 ml) and dimethylformamide (20 ml) was added chloroacetonitrile (4.76 ml) at room temperature. After stirring overnight, the precipitate was filtered off and the filtrate was poured into the mixture of water (30 ml) and dichloromethane (300 ml). The organic layer was separated, washed with brine and dried over magnesium sulfate. Evaporation of the solvent gave a residue, which was chromatographed on silica gel (450 ml) eluting with ethyl acetate to give (1,2,3-thiadiazol-5-yl)thioacetonitrile (10 g).

NMR (DMSO—$d_6$, $\delta$): 4.53 (2 H, s), 9.07 (1H, s).

Preparation 21-2)

Ethyl 2-[(1,2,3-thiadiazoI-5-Yl)thio]acetimidate dihydrochloride was obtained in substantially the same manner as that of Preparation 14-3).

NMR (DMSO—$d_6$, $\delta$) : 1.30 (3 H, t, J=7 Hz), 4.50 (2 H, q,
J=7 Hz), 4.56 (2 H, s), 9.14 (1 H, s).

Preparation 22-1)

To hydrazine monohydrate (168 ml) was added dropwise ethyl 2-(1-hydroxyethyl)acrylate (500 g) at −20° C. The reaction mixture was allowed to warm to room temperature and stirred overnight. After tetrahydrofuran (5 l) was added, the mixture was cooled to 3°-5° C. in an ice-bath. Sodium borohydride (527 g) was added portionwise under ice cooling. After the reaction mixture was stirred for 1 hour, boron trifluoride etherate was added dropwise while keeping the temperature below 20° C. After stirring overnight at room temperature, the mixture was quenched with methanol (5 l) and conc. hydrochloric acid (590 ml) under ice cooling. After stirring for a day at room temperature, the mixture was diluted with tetrahydrofuran (9 l), cooled to 10° C. in an ice-bath, the pH was adjusted to 8.5 with 4N sodium hydroxide. Benzyl chloroformate (1.49 l) was added dropwise while keeping pH at 8.5-9.0 with 4N aqueous sodium hydroxide in an ice-bath. After stirring for two hours, the mixture was diluted with ethyl acetate (9 l) and water (15 l). The aqueous layer was separated and extracted twice with ethyl acetate (5 l×2). The combined organic layer was washed with 1N hydrochloric acid (5 l), 5% aqueous sodium bicarbonate (5 l) and 10% aqueous sodium chloride (5 l), dried over magnesium sulfate and evaporated under reduced pressure. The residue was column chromatographed on silica gel (17.5 l), (eluent:hexane-ethyl acetate=1:1∼1:2) to give 1,2-bis(benzyloxycarbonyl)-4-(1-hydroxyethyl)pyrazolidine (733.1 g).

IR (Neat): 3300, 1725 cm$^{-1}$.

NMR (CDCl$_3$, $\delta$): 1.175 (3 H, d, J=6.27 Hz), 2.421 (1 H, m), 3.00-4.10 (5 H, m), 5.161 (4 H, s), 7.314 (10 H, s).

Preparation 22-2)

To a solution of oxalyl chloride (23 ml) in dichloromethane was added dropwise dimethyl sulfoxide (374 ml) while keeping the temperature below −50° C. After the mixture was stirred for 30 minutes at −50° C.∼−60° C., 1,2-bis(benzyloxycarbonyl)-4-(1-hydroxyethyl)pyrazolidine (675 g) was added dropwise below −50° C. After the mixture was stirred for 45 minutes at −50° C.∼−60° C., triethylamine (122 ml) was added dropwise below −50° C. The reaction mixture was allowed to warm to 0° C. and quenched with water (500 ml). The aqueous layer was separated and extracted twice with dichloromethane (200 ml×2). The combined organic layer was washed with 1N hydrochloric acid (200 ml×2), saturated sodium bicarbonte acid (200 ml), and 5% sodium chloride (200 ml), dried over magnesium sulfate, and evaporated under reduced pressure. The residue was chromatographed on silica gel (820 ml, hexane:ethyl acetate=2:1∼1:1) to give 1,2-bis(benzyloxycarbonyl)pyrazolidin-4-yl methyl ketone (61.5 g).

IR (Neat): 1720 cm$^{-1}$.

NMR (CDCl$_3$, $\delta$): 2.207 (3 H, s), 3.10-4.20 (4 H, m), 5.170 (4 H, s, 7.316 (10 H, s).

Preparation 22-3)

To a solution of 1,2-bis(benzyloxycarbonyl)pyrazolin-4-yl methyl ketone (96 g) and ethylpiperidine (448 ml) in dichloromethane (960 ml) was added dropwise trimethylsilyl triflate (55.8 ml) at 5° C. in an ice-bath. After the mixture was stirred for 20 hours at room temperature, the solution [A] prepared as mentioned below was added dropwise at room temperature. After stirring for 8 hours at room temperature, the reaction mixture was quenched with water. The aqueous layer was separated and extracted twice with dichloromethane. The combined organic layer was washed with 1N hydrochloric acid, saturated aqueous sodium bicarbonate and brine successively, dried over magnesium sulfate, and evaporated under reduced pressure. The residue was column chromatographed on silica gel (2 ) (eluent:hexane-ethyl acetate=1:1) to give (3S,4R)-4-[2-{1,2-bis(-benzyloxycarbonyl)pyrazolidin-4-yl}-2-oxoethyl]-3-[(1R)-1-t-butyldimethylsilyloxyethyl]-2-oxoazetidine (76.4 g).

Solution [A]

To a solution of (3R,4R)-4-acetoxy-3-[(R)-1-(t-butyl-dimethylsilyloxy)ethyl]-2-oxoazetidine (108.4 g) and ethylpiperidine (51.7 ml) in dichloromethane (960 ml) was added dropwise trimethylsilyl trifluoromethanesulfonate (72.9 ml) at −60° C. and the reaction mixture was allowed to warm to room temperature and stirred for 30 minutes.

IR (CHCl$_3$): 3400, 1750, 1710 cm$^{-1}$.
NMR (CDCl$_3$, δ): 0.063, 0.071 (6 H, s), 0.866 (9 H, s), 1.202 (3 H, d, J=6.23 Hz), 1.692 (1 H, m), 2.744 (1 H, dd, J=5.42 and 2.34 Hz), 2.60–3.10 (2 H, m), 3.39 (2 H, m), 3.95 (2 H, m), 4.05–4.20 (2 H, m), 5.161 (4 H, s), 7.315 (10 H, s).

Preparation 22-4)

To a solution of (3S,4R)-4-[2-{1,2-bis(benzyloxycarbonyl)pyrazolidin-4-yl}-2-oxoethyl]-3-[(1R)-1-t-butyldimethylsilyloxyethyl]-2-oxoazetidine (55 g) and 4N hydrochloric acid (68 ml) in methanol (900 ml) was added portionwise platinum oxide (18.5 g) under nitrogen atmosphere. The suspension was stirred under hydrogen atmosphere for 8 hours at room temperature. After then, the catalyst was filtered off and washed with water. The combined filtrate was evaporated to remove methanol and the residue was diluted with tetrahydrofuran and water. The pH was adjusted to 8.0 with 4N aqueous sodium hydroxide in an ice-bath and allyl chloroformate (29 ml) was added keeping pH at 8.0–8.5. After stirring for an hour at pH 8.0–8.5, the mixture was extracted three times with ethyl acetate. The combined organic layer was washed with 1N hydrochloric acid, saturated aqueous sodium bicarbonate and brine, dried over magnesium sulfate and evaporated under reduced pressure. The residue was chromatographed on silica gel (380 ml) (eluent:ethyl acetate) to give (3S,4R)-4-[4-allyloxycarbonylamino-3-(N-allyloxycarbonylaminomethyl-2-oxobutyl]-3-[(R)-1-hydroxyethyl]-2-oxoazetidine (28.52 g).

IR (CHCl$_3$): 3400, 1745, 1710 cm$^{-1}$.
NMR (CDCl$_3$, δ): 1.32 (3 H, d, J=4.66 Hz), 1.87 (1 H, m), 2.80–3.80 (7 H, m), 3.91 (1 H m), 4.14 (1 H, m), 4.53 (4 H, m), 5.19–5.34 (4 H, m), 5.60–6.00 (4H, m), 6.75 (1 H, br s).

Preparation 22-5)

To a solution of (3S,4R)-4-[4-allyloxycarbonylamino-3-(N-allyloxycarbonylaminomethyl)-2-oxobutyl]-3-[(1R)-1-hydroxyethyl]-2-oxoazetidine (459 mg) and pyridine (299 μl) in dichloromethane (10 ml) was added dropwise chlorotrimethylsilane (147 μl) and then allyl oxalyl chloride (199 μl) at −70° C. The reaction mixture was allowed to warm to −20° C., stirred for 30 minutes, and quenched with water (7 ml) and ethyl acetate (36 ml). The organic layer was separated and washed twice with water (7 ml) containing acetic acid (66 μl), water (7 ml), saturated aqueous sodium bicarbonate (7 ml) and brine (7 ml), dried over magnesium sulfate and evaporated under reduced pressure to give allyl 2-[(3S,4R)-4-[4-allyloxycarbonylamino-3-(N-allyloxycarbonylaminomethyl)-2-oxobutyl]-3-[(R)-1-hydroxyethyl]-2-oxoazetidin-1-yl]-2-oxoacetate. A mixture of the residue and triethyl phosphite (595 μl) in xylene (11 ml) was heated at 90° C. for 2 hours and then hydroquinone (64 mg) was added. The mixture was heated at 130° C.~135° C. for 2 hours, cooled to room temperature, and then diluted with ethyl acetate. The solution was washed twice with 10% potassium carbonate and brine, dried over magnesium sulfate and evaporated under reduced pressure. The residue was chromatographed on silica gel to give (604 mg) allyl (5R,6S)-3-[2-allyloxycarbonylamino-1-(N-allyloxycarbonylaminomethyl)ethyl]-6-[(1R)-1-(trimethylsilyloxy)ethyl]-7-oxo-1-azabicyclo-[3.2.0]hept-2-ene-2-carboxylate. To the above compound (604 mg) in acetic acid (126 μl) and tetrahydrofuran (6 ml) was added 1.0M tetrabutylammonium fluoride (1.1 ml) at 5° C. After stirring for 5 minutes, the reaction mixture was diluted with water (30 ml) and ethyl acetate (30 ml). The organic layer was separated and washed six times with water, dried over magnesium sulfate, and evaporated under reduced pressure. The residue was chromatographed on silica gel (50 ml) (eluent:hexane-ethyl acetate=1:1~0:1) to give allyl (5R,6S)-3-[2-allyloxycarbonylamino-1-(N-allyloxycarbonylaminomethyl)ethyl]-6-[(1R)-1-hydroxyethyl]-7-oxo-1-azabicyclo[3.2.0-]hept-2-ene-2-carboxylate (413 mg).

Preparation 22-6)

1,2-Bis(benzyloxycarbonyl)-4-(1-hydroxyethyl)-pyrazolidine (100 g) in methanol (900 ml) was treated with activated charcoal at room temperatures for 30 minutes. After removing activated charcoal platinum oxide (22 g) was added under nitrogen atmosphere. The suspension was stirred under hydrogen atmosphere for 17 hours. After the starting material and mono(benzyloxycarbonyl) compound was disappeared. The catalyst was filtered off under nitrogen atmosphere. The cake was washed with water (300 ml) and combined aqueous metanol layer was evaporated under reduced pressure. The pH of the residue and tetrahydrofuran (500 ml) was adjusted to 8.0 with 4N aqueous sodium hydroxide and allyl chloroformate was added dropwise while keeping pH at 8.0–9.0 with 4N aqueous sodium hydroxide in an ice-bath. After stirring for 1 hour at pH 8.0–8.3, the reaction mixture was extracted three times with ethyl acetate (250 ml×1 and 100 ml×2). The combined organic layer was washed with 1N hydrochloric acid, saturated sodium bicarbonate, and 10% sodium chloride, dried over magnesium sulfate and evaporated under reduced pressure. The residue was calumn chromatographed on silica gel to give 1-allyloxycarbonylamino-2-(N-allyloxycarbonylaminomethyl)-butan-3-ol (72.88 g).

Preparation 22-7)

To a solution of (3S,4R)-4-[2-{1,2-bis(benzyloxycarbonyl)pyrazolidin-4-yl}-2-oxoethyl]-3-[(1R)-1-t-butyldimethylsilyloxyethyl]-2-oxoazetidine (500 mg) and 1N hydrochloric acid (1.64 ml) in methanol (20 ml) was added platinum oxide (50 mg) under nitrogen atmosphere. The suspension was stirred under hydrogen atmosphere for 4 hours at room temperature. After then, the catalyst was filtered off and washed with water. After tetrahydrofuran (50 ml) and water (20 ml) was added, the pH was adjusted to 8.0 with saturated aqueous sodium bicarbonate in an ice bath and allyl chloroformate (348 ml) was added keeping pH at 8.0–8.5. After stirring for an hour at pH 8.0–8.5, the mixture was extracted three times with ethyl acetate.

The combined organic layer was washed with 1N hydrochloric acid, saturated aqueous sodium bicarbonate, and brine, dried over magnesium sulfate and evaporated under reduced pressure. The residue was chromatographed on silica gel to give (3S,4R)-4-[4-allyloxycarbonylamino-3-(N-allyloxycarbonylaminomethyl)-2-oxobutyl]-3-[(1R)-1-(t-butyldimethylsilyloxy)ethyl]-2-oxoazetidine (289 mg).

Preparation 23-1)

To a solution of ethyl (3R)-3-t-butyldimethylsilyloxy-2-methylidenebutanoate (130 g) in methanol (1.3 l) was added a solution of 30% methylamine in methanol (63 ml). The resulting mixture was allowed to stir at ambient temperature for 2 days. Evaporation of the solvent gave ethyl (2S,3R)-3-t-butyldimethylsilyloxy-2-(methylaminomethyl)butanoate (150.0 g).

NMR (DMSO—d$_6$, δ): 0.03 (6 H, s), 0.85 (9 H, s), 1.07 (3 H, d, J=6 Hz), 1.17 (3 H, t, J=7 Hz), 2.22 (3 H, s), 2.40–2.70 (3 H, m), 3.77–4.10 (3 H, m).

Preparation 23-2)

(2R,3R)-2-(N-Allyloxycarbonyl-N-methylaminomethyl)-3-t-butyldimethylsilyloxybutan-1-ol was obtained in substantially the same method as that of Preparation 2.

NMR (CDCl$_3$, δ): 0.07 (6 H, s), 0.90 (9 H, s), 1.24 (3 H, d, J=6 Hz), 1.57–7.178 (1H, m), 2.86 (3 H, s), 2.75–3.27 (2H, m), 3.50–3.70 (2 H, m), 3.84–4.00 (1 H, m), 4.50 –4.60 (2 H, m), 5.15–5.37 (2 H, m), 5.80–6.05 (1 H, m).

Preparation 23-3)

(2R,3R)-2-(N-Allyloxycarbonyl-N-methylaminomethyl)-3-t-butyldimethylsilyloxy-1-methanesulfonyloxybutane was obtained in substantially the same manner as that of Preparation 3.

NMR (CDCl$_3$, δ): 0.07 (6H, s), 0.90 (9 H, s), 1.20 (3 H, d, J=6 Hz), 2.09 (1 H, br s), 2.90 (3 H, s), 3.00 (3 H, s), 2.68–3.60 (2 H, m), 3.90–4.03 (1 H, m), 4.05–4.30 (2 H, m), 4.50–4.60 (2 H, m), 5.17–5.35 (2 H, m), 5.83–6.00 (1 H, m).

Preparation 23-4)

(2S,3R)-1-(N-Allyloxycarbonyl-N-methylamino)-2-allyloxycarbonylaminomethyl-3-t-butyldimethylsilyloxybutane (28.2 g) was obtained from (2R,3R)-2-(N-allyloxycarbonyl-N-methylaminomethyl-3-t-butyl-dimethylsilyloxy-1-methanesulfonyloxybutane (59 g) in substantially the same method as those of Preparations 4 and 5.

IR (Nujol): 3340, 1700 cm$^{-1}$.
NMR (CDCl$_3$, δ): 0.07 (6 H, s), 0.90 (9 H, s), 1.20 (3 H, d, J=6 Hz), 1.98 (1 H, br s), 2.90 (3 H, s), 2.80–3.45 (4 H, m), 3.60–4.00 (1 H, m), 4.41–4.55 (4 H, m), 5.00–5.30 (4 H, m), 5.73–6.00 (3 H, m).

Preparation 23-5)

To a stirred solution of (2S,3R)-1-(N-allyloxycarbonyl-N-methylamino)-2-allyloxycarbonylaminomethyl-3-t-butyldimethylsilyloxybutane (28.18 g) in ethyl acetate (500 ml) was added hydrochloric acid (6N, 17 ml), and the resulting mixture was stirred at ambient temperature for 2 hours. The reaction mixture was washed in turn with cold water, aqueous sodium hydrogen carbonate, and brine, and dried over magnesium sulfate. Evaporation of the solvent gave a residue which was chromatographed on silica gel (500 ml) eluting with a mixture of n-hexane and ethyl acetate (9:1–6:4, V/V) to give (2S,3R)-2-(N-allyloxycarbonyl-N-methylaminomethyl)-1-allyloxycarbonylamino-3-hydroxybutane (20.11 g).

IR (Nujol): 3350, 1680 cm$^{-1}$.
NMR (CDCl$_3$, δ): 1.27 (3 H, d, J=6.4 Hz), 1.70–1.90 (1 H, m), 2.93 (3 H, s), 3.00–3.60 (4 H, m), 3.70–4.05 (1 H, m), 4.50–4.63 (4 H, m), 5.10–5.40 (4 H, m), 5.80–6.05 (3 H, m).

Preparation 23-6)

(2S)-1-(N-Allyloxycarbonyl-N-methylamino)-2-(allyloxycarbonylamino)methylbutan-3-one was obtained in substantially the same method as that of Preparation 7.

NMR (CDCl$_3$, δ): 2.26 (3 H, s), 2.92 (3 H, s), 2.90–3.90 (5 H, m), 4.10–4.62 (4 H, m), 5.16–5.34 (4 H, m), 5.70 (1 H, br s), 5.80–6.02 (2 H, m).

Preparation 23-7)

To a solution of (2S)-1-(N-allyloxycarbonyl-N-methylamino)-2-(allyloxycarbonylaminomethyl)butan-3-one (14.59 g) in dichloromethane (110 ml) were added N-ethylpiperidine (13.5 ml) and trimethylsilyl trifluoromethanesulfonate (18.9 ml) at −10° C. and the resulting mixture was stirred at ambient temperature for 1 hour. To a solution of (3R,4R)-4-acetoxy-3-[(1R)-1-(t-butyldimethylsilyloxy)ethyl]-2-azetidinone (21.1 g) in dichloromethane (140 ml) were added N-ethylpiperidine (10.1 ml) and trimethylsilyl trifluoromethanesulfonate (14.2 ml) at −20° C. and the mixture was stirred at 0° C. for 1 hour. To a mixture of the latter solution and zinc bromide (44.05 g) was added the former solution at 0° C. and the resulting mixture was allowed to stir at ambient temperature for 2 hours. The reaction mixture was diluted with a mixture of water (800 ml) and ethyl acetate (800 ml). After adjusting pH to 0.7 with hydrochloric acid (6N), the mixture was allowed to stir at ambient temperature for 2 hours. The separated organic layer was washed in turn with water and brine. After adjusting pH to 7 with aqueous sodium hydrogen carbonate, the organic layer was washed with brine, dried over magnesium sulfate. Evaporation of the solvent gave a residue which was chromatographed on silica gel (1.5 l) eluting with a mixture of n-hexane and ethyl acetate (9:1–2:8, V/V) to give (3S,4R)-4-[(3S)-4-(N-allyloxycarbonyl-N-methylamino)-3-(allyloxycarbonylaminomethyl)-2-oxobutyl]-3-[(1R)-1-t-butyldimethylsilyloxyethyl]-2-oxoazetidine (19.42 g).

NMR (CDCl$_3$, δ): 0.07 (6 H, s), 0.87 (9 H, s), 1.21 (3 H, d, J=6.2 Hz), 2.77 (1 H, dd, J=1, 5 Hz), 2.90 (3 H, s), 2.85–4.10 (8 H, m), 4.10–4.23 (1 H, m), 4.19–4.62 (4 H, m), 5.10–5.35 (4 H, m), 5.75–6.00 (3 H, m), 6.47 (1 H, br s).

Preparation 23-8)

Allyl (5R,6S)-3-[(1S)-2-(N-allyloxycarbonyl-N-methylamino)-1-(allyloxycarbonylaminomethyl)ethyl]-6-[(1R)-1-(t-butyldimethylsilyloxy)ethyl]-7-oxo-1-azabicyclo[3.2.0]hept-2-ene-2-carboxylate (9.61 g) was obtained from (3S,4R)-4-[(3S)-4-(N-allyloxycarbonyl-N-methylamino)-3-(allyloxycarbonylaminomethyl)-2-oxobutyl] -3-[(1R)-1-t-butyldimethylsilyloxyethyl]-2-oxoazetidine (19.42 g) in substantially the same method as those of Preparations 9 and 10.

NMR (CDCl$_3$, δ): 0.07 (6 H, s), 0.90 (9 H, s), 1.22 (3 H, d, J=6 Hz), 2.92 (3 H, s), 2.78–3.67 (7 H, m), 3.87–4.28 (3 H, m}, 4.35–4.85 (6 H, m}, 5.08–5.52

(7 H, m), 5.71–6.08 (3 H, m).

Preparation 23-9)

Allyl (5R,6S)-3-[(1S)-2-(N-allyloxycarbonyl-N-methylamino)-1-(allyloxycarbonylaminomethyl)ethyl]-6-[(1R)-1-hydroxyethyl]-7-oxo-1-azabicyclo[3.2.0]hept-2-ene-2-carboxylate was obtained in substantially the same method as that of Preparation 11.

NMR (CDCl$_3$, δ): 1.24 (3 H, d, J=6 Hz), 2.91 (3 H, s), 2.85–3 44 (6 H, m), 3.44–3.73 (1 H, m), 3.95–4.22 (3 H, m}, 4.40–4.95 (6 H, m), 5.15–5.52 (7 H, m), 5.78–6.08 (3 H, m).

Preparation 24-1)

To a stirred solution of 1-allyloxycarbonylamino-2-(N-allyloxycarbonylaminomethyl)butan-3-ol (90.00 g) in N,N-dimethylformamide (800 ml) were added imidazole (85.51 g) and t-butyldimethylsilyl chloride (61.53 g). The resulting mixture was allowed to stand at ambient temperature for 14 hours. The mixture was diluted with ethyl acetate (2.4 l), washed successively with water (1.6 l) and brine (1 l), and dried over magnesium sulfate. Removal of the solvents gave a residue, which was chromatographed on silica gel (1 l) eluting with a mixture of n-hexane and ethyl acetate (9:1–7:3, V/V) to give 1-allyloxycarbonylamino-2-(N-allyloxycarbonylaminomethyl)-3-(t-butyldimethylsilyloxy)butane (115.40 g).

Preparation 24-2)

To a suspension of sodium hydride (60% dispersion in mineral oil) (12.6 g) in N,N-dimethylformamide (1 l) were added successively methyl iodide (63 ml) and a solution of 1-allyloxycarbonylamino-2-(N-allyloxycarbonylaminomethyl)-3-(t-butyldimethylsilyloxy)butane (115 g) in N,N-dimethylformamide (600 ml). After stirring at the same temperature for 30 minutes, to the mixture were added n-hexane (2 l), ethyl acetate (1 l), and water (5 l). The organic layer was separated, washed successively with water (1l×3) and brine (1 l), and dried over magnesium sulfate. Removal of the solvents gave 1-(N-allyloxycarbonyl-N-methylamino)-2-(N-allyloxycarbonyl-N-methylaminomethyl)-3-(t-butyldimethylsilyloxy)butane (123 g).

IR (CH$_2$Cl$_2$): 1690 cm$^{-1}$.
NMR (CDCl$_3$, δ): 0.05 (6 H, s), 0.89 (9 H, s), 1.08–1.24 (3 H, m), 1.99–2.19 (1 H, m), 2.90 (6 H, s), 3.04–3.58 (4 H, m), 3.85–4.00 (1 H, m), 4.58 (4 H, d, J=5.5 Hz), 5.15–5.41 (4 H, m), 5.81–6.10 (2 H, m).

Preparation 24-3)

To a stirred solution of 1-(N-allyloxycarbonyl-N-methylamino)-2-(N-allyloxycarbonyl-N-methylaminomethyl)-3-(t-butyldimethylsilyloxy)butane (123 g) in ethyl acetate (1.2 l) was added 6N-aqueous hydrochloric acid (240 ml) at ambient temperature. After stirring at the same temperature for 2.5 hours, to the mixture was added water (1 l) and the organic layer was separated. The organic layer was washed successively with 1N-aqueous sodium hydroxide (1 l), saturated aqueous ammonium chloride (500 ml), and brine (500 ml). After the solution was dried over magnesium sulfate, removal of the solvents gave a residue. The residue was chromatographed on silica gel (1 l) eluting with a mixture of n-hexane and ethyl acetate (95:5–40:60, V/V) to give 1-(N-allyloxycarbonyl-N-methylamino)-2-(N-allyloxycarbonyl-N-methylaminomethyl)-3-hydroxybutan-3-ol (83.18 g).

IR (CH$_2$Cl$_2$): 3720–3250, 1680 cm$^{-1}$.
NMR (CDCl$_3$, δ): 1.22 (3 H, d, J=6.7 Hz), 1.76–2.14 (1 H, m), 2.90 (1 H, s), 2.93 (6 H, s), 3.07–4.1 (5 H, m), 4.49–4.75 (4 H, m), 5.13–5.46 (4 H, m), 5.82–6.09 (2 H, m).

Preparation 24-4)

To a stirred solution of oxalyl chloride (25.5 ml) in dichloromethane (720 ml) were added successively dimethyl sulfoxide (45.1 ml), a solution of 1-(N-allyloxycarbonyl-N-methylamino)-2-(N-allyloxycarbonyl-N-methylaminomethyl)-3-hydroxybutan-3-ol (83.18 g) in dichloromethane (140 ml) and triethylamine (184.7 ml) at −60° C. After stirring at 0° C. for 30 minutes, the mixture was taken up into a mixture of ethyl acetate (2.6 l) and water (1 l). The organic layer was separated, washed successively with 1N aqueous hydrochloric acid (700 ml), saturated aqueous sodium hydrogen carbonate (700 ml) and brine (700 ml), and dried over magnesium sulfate. Removal of the solvents gave a residue, which was chromatographed on silica gel (1.5 l) eluting with a mixture of n-hexane and ethyl acetate (8:2–4:6, V/V) to give 1-(N-allyloxycarbonyl-N-methylamino)-2-(N-allyloxycarbonyl)-N-methylaminomethyl)butan-3-one (85.14 g).

IR (CH$_2$Cl$_2$): 1690, 1700 cm$^{-1}$.
NMR (CDCl$_3$, δ): 2.21 (3 H, s), 2.92 (6 H, s), 3.22–3.58 (5 H, m), 4.58 (4 H, d, J=5.5 Hz), 5.14–5.42 (4 H, m), 5.13–5.43 (4 H, m), 5.82–6.09 (2 H, m).

Preparation 24-5)

(3S,4R)-4-[4-(N-Allyloxycarbonyl-N-methylamino)-3-(N-allyloxycarbonyl-N-methylaminomethyl)-2-oxobutyl]-3-(1R)-1-t-butyldimethylsilyloxyethyl]-2-oxoazetidine was obtained in substantially the same manner as that of Preparation 8.

IR (CH$_2$Cl$_2$): 1760, 1700 cm$^{-1}$.
NMR (CDCl$_3$, δ): 0.07 (6 H, s), 0.87 (9 H, s), 1.21 (3 H, d, J=6.2 Hz), 2.55–3.06 (3 H, m), 2.90–2.92 (6 H, m), 3.21–5.19 (5 H, m), 3.91–4.02 (1 H, m), 4.11–4.26 (1 H, m), 4.56 (4 H, d, J=5.1 Hz), 5.18–5.39 (4 H, m), 5.81–6.04 (2 H, m), 6.04–6.32 (1 H, br s).

Preparation 24-6)

Allyl (5R,6S)-3-[2-(N-allyloxycarbonyl-N-methylamino)-1-(N-allyloxycarbonyl-N-methylaminomethyl)-6-[(1R)-1-t-butyldimethylsilyloxyethyl]-7-oxo-1-azabicyclo[3.2.0]hept-2-ene-2-carboxylate (12.7 g) was obtained from (3S,4R)-4-[4-(N-allyloxycarbonyl-N-methylamino)-3-(N-allyloxycarbonyl-N-methylaminomethyl)-2-oxobutyl]-3-[(1R)-1-t-butyldimethylsilyloxyethyl]-2-oxoazetidine (81.52 g) in substantially the same manner as those of Preparations 9 and 10.

IR (CH$_2$Cl$_2$): 1780, 1700 cm$^{-1}$.
NMR (CDCl$_3$, δ): 0.07 (6 H, s), 0.88 (9 H, s), 1.21 (3 H, d, J=6.2 Hz), 2.74–3.90 (8 H, m), 2.91 (6 H, s), 3.94–4.87 (8 H, m), 5.13–5.52 (6 H, m), 5.80–6.07 (3 H, m).

Preparation 24-7)

Allyl (5R,6S)-3-[2-(N-allyloxycarbonyl-N-methylamino)-1-(N-allyloxycarbonyl-N-methylaminomethyl)-6-[(1R)-1-hydroxyethyl]-7-oxo-1-azabicyclo[3.2.0]hept-2-ene-2-carboxylate (12.7 g) was obtained in substantially the same manner as that of Preparation 11.

IR ($CH_2Cl_2$): 1770, 1690 cm$^{-1}$.
NMR ($CDCl_3$, δ): 1.31 (3 H, d, J=6.4 Hz), 2.71–3.92 (8 H, m), 2.86 (3 H, s), 2.91 (3 H, s), 4.04–4.92 (8 H, m), 5.13–5.53 (6 H, m), 5.79–6.21 (3 H, m).

Preparation 25-1)

To a solution of 2-cyano-3-hydroxy-1-pentene (10 g) in methanol (100 ml) was added benzylamine (10 ml). After stirring for 8 hours under reflux, the solvent was evaporated, and the residue was chromatographed on silica gel with eluting a mixture of n-hexane and ethyl acetate (1:1, V/V) to give 1-benzylamino-2-cyano-3-hydroxypentane (10 g).

IR (Neat): 3300, 2240 cm$^{-1}$.
NMR ($CDCl_3$, δ): 0.97 (3 H, t, J=7.5 Hz), 1.4–1.9 (2 H, m), 2.5–3.3 (3 H, m), 3.7–3.9 (3 H, m).

Preparation 25-2)

To a solution of 1-benzylamino-2-cyano-3-hydroxypentane (1.0 g) in 5% ammonia-methanol solution (20 ml) was added Raney Nickel (W2, 5g). After stirring under atmospheric pressure of hydrogen at room temperature for 4 hours, the catalyst was filtered off and to the filtrate were added ammonium formate (1.4 g) and 10% palladium on carbon (1 g, 50% wet). After stirring for 1 hour under reflux, the catalyst was filtered off and the filtrate was evaporated to give 1-amino-2-aminomethyl-3-hydroxypentane (0.91 g).

IR (Neat): 3200–3300 cm$^{-1}$.
NMR (DMSO—$d_6$, δ): 0.86 (3 H, t, J=7 Hz), 1.3–1.5 (3 H, m).

Preparation 25-3)

2-(1-Oxopropyl)-1,3-bis(allyloxycarbonylamino)propane (1.1 g) was 1-allyloxycarbonylamino-2-(N-allyloxycarbonylaminomethyl)butan-3-one was obtained from 1-amino-2-aminomethyl-3-hydroxypentane in substantially the same manner as those of Preparations 5 and 7.

IR (Neat): 3350, 1700 cm$^{-1}$.
NMR ($CDCl_3$, δ): 1.05 (3 H, t, J=7 Hz), 2.56 (2 H, q, J=7 Hz), 2.8–3.0 (1 H, m), 3.2–3.4 (2 H, m), 3.4–3.6 (2 H, m), 4.5–4.6 (4 H, m), 5.1–5.4 (4 H, m), 5.58 (1 H, br s), 5.8–6.0 (2 H, m).

Preparation 25-4)

(3S,4R)-4-[5-Allyloxycarbonylamino-4-(N-allyloxycarbonylaminomethyl)-3-oxopentyl]-3-[(R)-1-(t-butyldimethylsilyloxy)ethyl]-2-oxoazetizine was obtained in substantially the same manner as that of Preparation 8.

IR (Neat): 3300, 1750, 1700 cm$^{-1}$.
NMR ($CDCl_3$, δ): 0.08 (6 H, s), 0.84 (9 H, s), 1.1–1.2 (6 H, m), 2.6–2.9 (1 H, m), 2.9–3.6 (7 H, m), 4.3–4.5 (4 H, m), 5.0–5.3 (4 H, m), 5.3–5.9 (4 H, m), 6.29, 6.80 (1 H, each br s).

Preparation 25-5)

Allyl (5R,6S)-3-[2-allyloxycarbonylamino-1-(N-allyloxycarbonylaminomethyl)ethyl]-6-[(1R)-1-(t-butyldimethylsilyloxy)ethyl]-4-methyl-7-oxo-1-azabicyclo[3.2.0]-hept-2-ene-2-carboxylate was obtained in substantially the same manner as those of Preparations 9 and 10.

IR (Neat): 1770, 1710 cm$^{-1}$.
NMR ($CDCl_3$, δ): 0.08 (6 H, s), 0.88 (9 H, s), 1.1–1.3 (6 H, m), 3.0–3.7 (5 H, m), 4.4–4.8 (4 H, m), 5.2–5.4 (4 H, m), 5.8–6.0 (2 H, m).

Preparation 25-6)

(5R,6S)-3-[2-Allyloxycarbonylamino-1-(N-allyloxycarbonylaminomethyl)ethyl]-6-[(R)-1-hydroxyethyl]-4-methyl-7-oxo-1-azabicyclo[3.2.0]hept-2-ene-2-carboxylate was obtained in substantially the same manner as that of Preparation 11.

IR (Neat): 3350, 1780, 1710 cm$^{-1}$.
NMR ($CDCl_3$, δ): 1.1–1.3 (6 H m). 3.0–3.8 (5 H, m), 4.4–4.8 (4 H, m), 5.1–5.4 (4 H, m), 5.8–6.0 (2 H, m).

Preparation 25-7)

Allyl (5R,6S)-3-[2-amino-1-(aminomethyl)ethyl]-6-[(R)-1-hydroxyethyl]-4-methyl-7-oxo-1-azabicyclo[3.2.0]hept-2-ene-2-carboxylate was obtained in substantially the same manner as that of former part of Example 1.

IR (Nujol): 1750 cm$^{-1}$.
NMR (D20, δ): 1.1–1.4 (6 H, m), 3.0–3.8 (5 H, m).

EXAMPLE 1

To a solution of 741 mg of allyl (5R,6S)-3-[2-allyloxycarbonylamino-1-(N-allyloxycarbonylaminomethyl)ethyl]-6-[(R)-1-hydroxyethyl]-7-oxo-1-azabicyclo[3.2.0]hept-2-ene-2-carboxylate in 9.25 ml of tetrahydrofuran and 3.07 ml of ethanol were added successively 163 mg of triphenylphosphine, 870 mg of dimedone, 0.089 ml of acetic acid and 143 mg of tetrakis(triphenylphosphine)-palladium at room temperature under nitrogen. The mixture was stirred at 30° C. for a few minutes, and then stirring was continued at room temperature for 30 minutes. After a pale yellow precipitate was deposited, 2.2 ml of ethyl acetate was added. The precipitate was filtrated and washed with ethyl acetate and dichloromethane under nitrogen, and dissolved in pH 6.86 buffer solution. 399 mg of Benzyl formimidate hydrochloride was added to the solution at 0° C., while the pH was kept at 8.5. After stirring for 1.5 hours at pH 7.0, the reaction mixture was washed five times with 30% tetrahydrofuran in ethyl acetate while the pH was kept at pH 7. Purification was carried out by a column chromatography on "Diaion HP-20" (trademark, made by Mitsubishi Chemical Industries) (eluent: water followed by 2% acetonitrile in water) and silica gel (eluent: 0–30% water in acetonitrile gradiently) successively to give 99 mg of [5R,6S)-6-[(R)-1-hydroxyethyl]-3-[3,4,5,6-tetrahydropyrimidin-5-yl]-7-oxo-1-azabicyclo[3.2.0]hept-2-ene-2-carboxylic acid.

IR ($CHCl_3$): 3150, 2910, 2845, 1750, 1675, 1580, 1455, 1378 cm$^{-1}$.
NMR ($D_2O$, δ): 1.25 (3 H, d, J=6.3 Hz), 2.85 (2 H, d, J=9.0 Hz), 3.27–4.25 (11 H, m), 7.91 (1 H, s).

EXAMPLE 2

(5R,6S)-6-[(R)-1-Hydroxyethyl]-3-[2-methyl-3,4,5,6-tetrahydropyrimidin-5-yl]-7-oxo-1-azabicyclo[3.2.0]-hept-2-ene-2-carboxylic acid was obtained in 22.3 % yield in substantially the same manner as that of Example 1 by using ethyl acetimidate hydrochloride instead.

IR (Nujol): 3000–3700 (br), 1755, 1650, 1575 cm$^{-1}$.
NMR (D20, δ): 1.25 (3 H, d, J=6 Hz), 2.18 (3 H, s), 2.84 (2 H, d, J=9 Hz), 3.10–4.35 (8 H, m).

EXAMPLE 3

(5R,6S)-6-[(R)-1-Hydroxyethyl]-3-[2-methoxymethyl-3,4,5,6-tetrahydropyrimidin-5-yl]-7-oxo-1-azabicyclo-[3.2.0]hept-2-ene-2-carboxylic acid was obtained in 32.7% yield in substantially the same manner as that of Example 1 by using ethyl 2-methoxyacetoimidate hydrochloride instead.

IR (Nujol): 2910, 1751, 1662, 1579, 1275, 1113 cm$^{-1}$.
NMR (D$_2$O, δ): 1.27 (3 H, d, J=6.3 Hz), 2.86 (2 H, d, J=9.0 Hz), 3.45 (3 H, s), 3.2–4.3 (8 H, m), 4.31 (2 H, s).

EXAMPLE 4

(5R,6S)-6-[(R)-1-Hydroxyethyl]-3-[2-carbamoylmethyl-3,4,5,6-tetrahydropyrimidin-5-yl]-7-oxo-1-azabicyclo[3.2.0]hept-2-ene-2-carboxylic acid was obtained in 15.9% yield in substantially the same manner as that of Example 1 by using O-ethyl 2-carbamoylacetimidate hydrochloride instead.

IR (Nujol): 3650–2500 (br), 1750, 1690, 1630, 1580 cm$^{-1}$.
NMR (D$_2$O, δ): 1.27 (3 H, d, J=6.3 Hz), 2.86 (2 H, d, J=9.0 Hz), 3.1–4.3 (8 H, m), 4.68 (2 H, s).

EXAMPLE 5-1)

To a stirred solution of allyl (5R,6S)-3-[(1S)-2-(N-allyloxycarbonyl-N-methylamino)-1-(allyloxycarbonylaminomethyl)ethyl]-6-[(1R)-1-hydroxyethyl]-7-oxo-1-azabicyclo-[3.2.0]hept-2-ene-2-carboxylate (0.8 g) and triphenylphosphine (0.17 g) in a mixture of tetrahydrofuran (25 ml) and ethanol (8.3 ml) were added successively acetic acid (0.56 ml), tetrakis(triphenylphosphine)palladium(0) (0.15 g) and tributyltin hydride (1.75 ml) at 30° C. under nitrogen atmosphere. After stirring for 15 minutes, the resulting precipitates were collected by filtration, washed with ethyl acetate and dissolved in phosphate buffer (pH 6.86, 50 ml). To the solution was added by portions ethyl 2-methoxyacetimidate hydrochloride (0.25 g) while adjusting pH of the solution to around 8.5 with 10% aqueous potassium carbonate at 15° C. After stirring for 30 minutes at pH 8.5, the pH was adjusted to 7 with 6N hydrochloric acid and the reaction mixture was washed 4 times with a mixture of tetrahydrofuran and ethyl acetate (3:7, V/V). Evaporation of the solvent gave a residue which was chromatographed on nonionic adsorption resin, Diaion HP-20 (Trademark, made by Mitsubishi Chemical Industries) (150 ml) eluting with a mixture of water and acetonitrile (100:0–95:5, V/V). Lyophilization of the eluate gave (5R,6S)-3-[(1S)-1-(2-methoxyacetoimidoylamino)methyl-2-(methyl-ammonio)ethyl]-6-[(1R)-1-hydroxyethyl]-7-oxo-1-azabicyclo[3.2.0]hept-2-ene-2-carboxylic acid hydrogen carbonate (179 mg).

IR (Nujol): 3200, 1750 cm$^{-1}$.
NMR (D$_2$O, δ): 1.28 (3 H, d, J=6 Hz), 2.76 (3 H, s), 2.80–3.35 (4 H, m), 3.35–3.67 (6 H, m), 4.10–4.35 (3 H, m), 4.37 (2 H, s).

Elution was continued and the eluate was evaporated to give crude object (170 mg), which was chromatographed on silica gel (150 ml) eluting with a mixture of acetonitrile and water (10:0–7:3, V/V). Lyophilization of the eluate gave (5R,6S)-6-[(1R)-1-hydroxyethyl]-3-[(5R)-1-methyl-2-methoxymethyl-1,4,5,6-tetrahydropyrimidin-5-yl]-7-oxo-1-azabicyclo[3.2.0]hept-2-ene-2-carboxylic acid (160 mg).

IR (Nujol): 3200, 1750, 1660, 1590 cm$^{-1}$.
NMR (D$_2$O, δ): 1.28 (3 H, d, J=6 Hz), 2.87 (2 H, d, J=10 Hz) 3.09 (3 H, s), 3.30–3.60 (5 H, m), 3.51 (3 H, s), 3.80–4.05 (1 H, m), 4.09–4.30 (2 H m) 4.48 (2 H, s).

The following compounds were obtained in substantially the same manner as that of Example 5-1).

EXAMPLE 5-2)

(5R,6S)-3-[(1S)-1-(2-Carbamoylacetimidoylamino)-methyl-2-(methylammonio)ethyl]-6-[(1R)-1-hydroxyethyl]-7-oxo-1-azabicyclo[3.2.0]hept-2-ene-2-carboxylic acid hydrogen carbonate IR (Nujol): 3200, 1750, 1690 cm$^{-1}$.
NMR (D$_2$O, δ): 1.28 (3 H, d, J=6 Hz), 2.76 (3 H, s), 2.70–3.10 (2 H, m), 3.10–3.25 (2 H, m), 3.40–3.60 (3 H, m), 4.05–4.30 (3 H, m).

(5R,6S)-6-[(1R)-1-Hydroxyethyl]-3-[(5R)-1-methyl-2-carbamoylmethyl-1,4,5,6-tetrahydropyrimidin-5-yl]-7-oxo-1-azabicyclo[3.2.0]hept-2-ene-2-carboxylic acid IR (Nujol): 3200, 1750, 1660, 1570 cm$^{-1}$.
NMR (D$_2$O, δ): 1.28 (3 H, d, J=6 Hz), 2.90 (2 H, d, J=9 Hz), 3.19 (3 H, s), 3.30–3.65 (5 H, m), 3.80–4.05 (1 H, m), 4.10–4.30 (2 H, m).

EXAMPLE 5-3)

(5R,6S)-6-[(1R)-1-Hydroxyethyl]-3-[(5R)-1-methyl-2-acetamidomethyl-1,4,5,6-tetrahydropyrimidin-5-yl]-7-oxo-1-azabicyclo[3.2.0]hept-2-ene-2-carboxylic acid IR (Nujol): 3250 1750 1660 1580 cm$^{-1}$.
NMR (D$_2$O, δ): 1.28 (3 H, d, J=6 Hz), 2.11 (3 H, s), 2.86 (2 H, d, J=9 Hz), 3.21 (3 H, s), 3.25–3.65 (5 H, m), 3.80–4.05 (1 H, m), 4.05–4.18 (2 H, m), 4.32 (2 H, d, J=5 Hz).

EXAMPLE 5-4)

(5R,6S)-6-[(1R)-1-Hydroxyethyl]-3--[(5R)-1-methyl-2-difluoromethylthiomethyl-1,4,5,6-tetrahydropyrimidin-5-yl]-7-oxo-1-azabicyclo[3.2.0-]hept-2-ene-2-carboxylic acid IR (Nujol): 3360, 1770, 1660, 1620 cm$^{-1}$.
NMR (D$_2$O, δ): 1.28 (3 H, d, J=6 Hz), 2.88 (2 H, d, J=9 Hz), 3.27 (3 H, s), 3.30–3.60 (5 H, m), 3.80–4.00 (1 H, m), 4.04 (2 H, s), 4.10–4.27 (2 H, m), 7.16 (1 H, t, J=55 Hz).

(5R,6S)-3-[(1S)-1-(2-Difluoromethylthiomethylacetimidoylamino)methyl-2-methylammonio)ethyl]-6-[(1R)-1-hydroxyethyl]-7-oxo-1-azabicyclo[3.2.0-]hept-2-ene-2-carboxylic acid hydrogen carbonate IR (Nujol) 3200, 1760, 1690, 1640 cm$^{-1}$.
NMR (D$_2$O, δ): 1.29 (3 H, d, J=6 Hz), 2.75 (3 H, s), 2.76–3.05 (2 H, m), 3.10–3.30 (2 H, m), 3.38–3.55 (3 H, m), 3.89 (2 H, s), 4.15–4.30 (3 H, m), 7.13 (1 H, t, J=56 Hz).

EXAMPLE 6-1)

(5R,6S)-3-[(1S)-1-(2-Difluoromethylthiomethylacetimidoylamino)methyl-2-methylammonio)ethyl]-6-[(1R)-1-hydroxyethyl]-7-oxo-1-azabicyclo[3.2.0-]hept-2-ene-2-carboxylic acid hydrogen carbonate (0.30 g) was dissolved in phosphate buffer (pH 6.86, 10 ml) and the pH was adjusted to around 8.5 with 10% aqueous potassium carbonate. The resulting solution was allowed to stir at ambient temperature for 2 hours.

Evaporation of the solvent gave a residue, which was chromatographed on nonionic adsorption resin, Diaion HP-20 eluting with a mixture of water and acetonitrile (100:0–95:5, V/V) to give (5R,6S)-6-[(1R)-1-hydroxyethyl]-3-[(5R)-1-methyl-2-difluoromethylthiomethyl-1,4,5,6-tetrahydropyrimidin-5-yl]-7-oxo-1-azabicyclo[3.2.0]hept-2-ene-2-carboxylic acid (0.16 g).

IR (Nujol): 3360, 1770, 1660, 1620 cm$^{-1}$.

The following compounds were obtained in substantially the same manner as that of Example 6-1).

EXAMPLE 6-2)

(5R,6S)-3-[(1S)-1-(2-Carbamoylacetimidoylamino)methyl-2-(methylammonio)ethyl]-6-[(1R)-1-hydroxyethyl]-7-oxo-1-azabicyclo[3.2.0]hept-2-ene-2-carboxylic acid hydrogen carbonate IR (Nujol): 3200, 1750, 1690 cm$^{-1}$.

EXAMPLE 6-3)

(5R,6S)-3-[(1S)-1-(2-Methoxyacetimidoylamino)methyl-2-(methylammonio)ethyl]-6-[(1R)-1-hydroxyethyl]-7-oxo-1-azabicyclo[3.2.0]hept-2-ene-2-carboxylic acid hydrogen carbonate IR (Nujol): 3200, 1750 cm$^{-1}$.

The following compounds were obtained in substantially the same manner as that of Example 1.

EXAMPLE 7-1)

(5R,6S)-6-[(1R)-1-Hydroxyethyl]-3-(1,3-dimethyl-1,4,5,6-tetrahydro-5-pyrimidinio)-7-oxo-1-azabicyclo[3.2.0]hept-2-ene-2-carboxylate IR (Nujol) 3570-2750, 1740 cm$^{-1}$.

NMR (D$_2$O, δ): 1.26 (3 H, d, J=6 Hz), 2.84 (2 H, d, J=9 Hz), 3.00–3.58 (5 H, m), 3.17 (6 H, s), 3.66–4.33 (3 H, m), 7.84 (1 H, s).

EXAMPLE 7-2)

(5R,6S)-6-[(1R)-1-Hydroxyethyl]-3-[1,3-dimethyl-2-(methylthiomethyl)-1,4,5,6-tetrahydro-5-pyrimidinio]-7-oxo-1-azabicyclo[3.2.0]hept-2-ene-2-carboxylate IR (Nujol) 1750, 1630, 1580 cm$^{-1}$.

NMR (D$_2$O, δ): 1.28 (3 H, d, J=6.4 Hz), 2.30 (3 H, s), 2.87 (2 H, d, J=9.2 Hz), 3.33 (6 H, s), 3.33–3.39 (1 H, m), 3.53–3.56 (4 H, m), 3.78 (2 H, s), 3.80–4.25 (3 H, m).

The following compounds were obtained in substantially the same manner as that of the latter part of Example 1.

EXAMPLE 8-1)

(5R,6S)-3-(2-Carbamoylmethyl-1,4,5,6-tetrahydropyrimidin-5-yl)-6-[(1R)-1-hydroxyethyl]-4-methyl-7-oxo-1-azabicyclo[3.2.0]hept-2-ene-2-carboxylic acid IR (Nujol) 3300, 1750 cm$^{-1}$.

NMR (D$_2$O, δ): 1.28 (3 H, d, J=6 Hz), 1.31 (3 H, d, J=6 Hz), 3.1–4.0 (11 H, m), 4.0–4.3 (2 H, m)

EXAMPLE 8-2)

(5R,6S)-3-(2-Methoxymethyl-1,4,5,6-tetrahydropyrimidin-5-yl)-6-[(1R)-1-hydroxyethyl]-4-methyl-7-oxo-1-azabicyclo[3.2.0]hept-2-ene-2-carboxylic acid IR (Nujol): 1750 cm$^{-1}$.

NMR (D$_2$O, δ): 1.2–1.3 (6 H, m), 3.1–3.8 (7 H, m), 3.45 (3 H, s), 4.1–4.4 (2 H, m), 4.33 (2 H, s).

The following compounds were obtained in substantially the same manner as that of Example 1.

EXAMPLE 9-1)

(5R,6S)-6-[(1R)-1-Hydroxyethyl]-3-[2-(N-methylcarbamoylmethyl)-1,4,5,6-tetrahydropyrimidin-5-yl]-7-oxo-1-azabicyclo[3.2.0]hept-2-ene-2-carboxylic acid IR (Nujol): 1745, 1650 cm$^{-1}$.

NMR (D$_2$O, δ): 1.28 (3 H, d, J=6.35 Hz), 2.77 (3 H, s), 2.89 (2 H, d, J=9.66 Hz), 3.33–3.88 (5 H, m), 3.75–3.95 (1 H, m), 4.12–4.30 (2 H, m).

EXAMPLE 9-2)

(5R,6S)-3-[2-{N-(2-Hydroxyethyl)carbamoylmethyl}-1,4,5,6-tetrahydropyrimidin-5-yl]-6-[(1R)-1-hydroxyethyl]-7-oxo-1-azabicyclo[3.2.0]hept-2-ene-2-carboxylic acid (Nujol): 1745, 1645 cm$^{-1}$.

NMR (D$_2$O, δ): 1.28 (3 H, d, J=6.37 Hz), 2.89 (2 H, d, J=10.1 Hz), 3.35–3.90 (10 H, m), 4.11–4.29 (2 H, m).

EXAMPLE 9-3)

(5R,6S)-3-[2-(N-Allylcarbamoylmethyl)-1,4,5,6-tetrahydropyrimidin-5-yl]-6-[(1R)-1-hydroxyethyl]-7-oxo-1-azabicyclo[3.2.0]hept-2-ene-2-carboxylic acid IR (Nujol): 1740 cm$^{-1}$.

NMR (D$_2$O, δ): 1.28 (3 H, d, J=6.35 Hz), 2.89 (2 H, d, J=9.8 Hz), 3.35–3.86 (10 H, m), 4.12–4.26 (2 H, m), 5.15–5.24 (2 H, m), 5.77–5.97 (1 H, m).

EXAMPLE 9-4)

(5R,6S)-6-[(1R)-1-Hydroxyethyl]-3-[2-(imidazol-2-ylthiomethyl)-1,4,5,6-tetrahydropyrimidin-5-yl]-7-oxo-1-azabicyclo[3.2.0]hept-2-ene-2-carboxylic acid IR (Nujol): 1750, 1660, 1580 cm$^{-1}$.

NMR (D$_2$O, δ): 1.28 (3 H, d, J=6.38 Hz), 2.78 (2 H, d, J=9 24 Hz), 3.23–3.53 (5 H, m), 3.60–3.82 (1 H, m), 3.82 (2 H, s), 4.07–4.28 (2 H, m), 7.25 (2 H, s).

EXAMPLE 9-5)

(5R,6S)-6-[(1R)-1-Hydroxyethyl]-3-[2-{(1-methylimidazol-2-yl)thiomethyl}-1,4,5,6-tetrahydropyrimidin-5-yl]-7-oxo-1-azabicyclo[3.2.0]hept-2-ene-2-carboxylic acid IR (Nujol): 1745, 1650, 1610, 1570 cm$^{-1}$.

NMR (D$_2$O, δ): 1.28 (3 H, d, J=6.35 Hz), 2.80 (2 H, d, J=9.19 Hz), 3.23–3.80 (9 H, m), 3.78 (2 H, s), 7.15 (1 H, s), 7.32 (1 H, s).

EXAMPLE 9-6)

(5R,6S)-6-[(1R)-1-Hydroxyethyl]-3-[2-(N-methanesulfonylaminomethyl)-1,4,5,6-tetrahydropyrimidin-5-yl]-7-oxo-1-azabicyclo[3.2.0]hept-2-ene-2-carboxylic acid IR (Nujol): 1740, 1660, 1640, 1570 cm$^{-1}$.

NMR (D$_2$O, δ): 1.28 (3 H, d, J=6.37 Hz), 2.89 (2 H, d, J=9.45 Hz), 3.16 (3 H, s), 3.35–3.60 (5 H, m), 3.85 (1 H, m), 4.10–4.26 (2 H, m), 4.22 (2 H, s).

EXAMPLE 9-7)

(5R,6S)-6-[(1R)-1-Hydroxyethyl]-3-[2-(N-methoxycarbonylaminomethyl)-1,4,5,6-tetrahydropyrimidin-5-yl]-7-oxo-1-azabicyclo[3.2.0]hept-2-ene-2-carboxylic acid IR (Nujol): 1750, 1700 cm$^{-1}$.

NMR (D$_2$O, δ): 1.28 (3 H, d, J=6.36 Hz), 2.89 (2 H, d, J=9.34 Hz), 3.31–3.90 (6 H, m), 3.72 (3 H, s), 4.11–4.29 (2 H, m), 4.17 (2 H, s).

EXAMPLE 9-8)

(5R,6S)-6-[(1R)-1-Hydroxyethyl]-3-[2-(nicotinylaminomethyl)-1,4,5,6-tetrahydropyrimidin-5-yl]-7-oxo-1-azabicyclo[3.2.0]hept-2-ene-2-carboxylic acid IR (Nujol): 1750, 1650, 1570 cm$^{-1}$.

NMR (D$_2$O, δ): 1.27 (3 H, d, J=6.37 Hz), 2.90 (2 H, d, J=9.36 Hz), 3.34–4.25 (8 H, m), 4.44 (2 H, s), 7.59–7.66 (1 H, m), 8.25–8.31 (1 H, m), 8.72–8.76 (1 H, m), 8.97–8.99 (1 H, m).

EXAMPLE 9-9)

(5R,6S)-6-[(1R)-1-Hydroxyethyl]-3-[2-{(2-methylthionicotinyl)aminomethyl) -1,4,5,6-tetrahydropyrimidin-5-yl]-7-oxo-1-azabicyclo[3.2.0]hept-2-ene-2-carboxylic acid IR (Nujol): 1750, 1640, 1580 cm$^{-1}$.

NMR (D$_2$O, δ): 1.26 (3 H, d, J=6.37 Hz), 2.55 (3 H, s), 2.93 (2 H, d, J=9.18 Hz), 3.35–4.25 (8 H, m), 4.38 (2 H, s), 7.26–7.32 (1 H, m), 7.90–7.95 (1 H, m), 8.53–8.56 (1 H, m).

EXAMPLE 9-10)

(5R,6S)-6-[(1R)-1-Hydroxyethyl]-3-[2-{(1,2,3-thiadiazol-5-yl)thiomethyl}-1,4,5,6-tetrahydropyrimidin-5-yl]-7-oxo-1-azabicyclo[3.2.0]hept-2-ene-2-carboxylic acid IR (Nujol): 1750, 1660, 1580 cm$^{-1}$.

NMR (D$_2$O, δ): 1.28 (3 H, d, J=6.38 Hz), 2.79 (2 H, d, J=9.40 Hz), 3.31–4.25 (10 H, m), 8.86 (1 H, s).

EXAMPLE 10-1)

(5R,6S)-6-[(1R)-1-Hydroxyethyl]-3-[2-(N-methylcarbamoyloxymethyl)-1,4,5,6-tetrahydropyrimidin-5-yl]-7-oxo-1-azabicyclo[3.2.0]hept-2-ene-2-carboxylic acid IR (Nujol): 1725, 1662, 1580 cm$^{-1}$.

NMR (D$_2$O, δ): 1.28 (3 H, d, J=6.4 Hz), 2.74 (3 H, s), 2.89 (2 H, d, J=9.4 Hz), 3.3–3.75 (5 H, m) 3.75–4.0 (1 H, m), 4.05–4.4 (2 H, m), 4.88 (2 H, s).

EXAMPLE 10-2)

(5R,6S)-6-[(1R)-1-Hydroxyethyl]-3-(2-chloromethyl-1,4,5,6-tetrahydropyrimidin-5-yl)-7-oxo-1-azabicyclo[3.2.0]hept-2-ene-2-carboxylic acid IR (Nujol): 1744, 1680, 1565 cm$^{-1}$.

NMR (D$_2$O, δ): 1.26 (3 H, d, J=6.4 Hz), 2.83 (2 H, d, J=9.1 Hz), 3.2–4.5 (10 H, m).

EXAMPLE 10-3)

(5R,6S)-6-[(1R)-1-Hydroxyethyl]-3-[2-(2-hydroxyethyl)-1,4,5,6-tetrahydropyrimidin-5-yl]-7-oxo-1-azabicyclo[3.2.0]hept-2-ene-2-carboxylic acid IR (Nujol): 1755, 1660, 1570 cm$^{-1}$.

NMR (D$_2$O, δ): 1.25 (3 H, d, J=6.2 Hz), 2.63 (2 H, t, J=6 Hz), 2.88 (2 H, d, J=9.2 Hz), 3.16–4.42 (10 H, m).

EXAMPLE 10-4)

(5R,6S)-6-[(1R)-Hydroxyethyl]-3-(2-carbamoyloxymethyl-1,4,5,6-tetrahydropyrimidin-5-yl)-7-oxo-1-azabicyclo[3.2.0]hept-2-ene-2-carboxylic acid IR (Nujol): 1738, 1720, 1657, 1620, 1570 cm$^{-1}$.

NMR (D$_2$O, δ): 1.28 (3 H, d, J=6.2 Hz), 2.88 (2 H, d, J=9.6 Hz), 3.21–3.75 (6 H, m), 3.76–4.0 (1 H, m), 4.10–4.31 (2 H, m).

EXAMPLE 10-5)

(5R,6S)-6-[(1R)-1-Hydroxyethyl]-3-[2-{2-(3-hydroxyazetidin-1-yl)-2-oxoethyl}-1,4,5,6-tetrahydropyrimidin-5-yl]-7-oxo-1-azabicyclo[3.2.0]hept-2-ene-2-carboxylic acid IR (Nujol): 1750, 1645, 1580 cm$^{-1}$.

NMR (D$_2$O, δ): 1.26 (3 H, d, J=6.1 Hz), 2.83 (2 H, d, J=9.1 Hz), 3.1–4.50 (15 H, m).

EXAMPLE 10-6)

(5R,6S)-6-[(1R)-1-Hydroxyethyl]-3-[2-(3-pyridylmethyl)-1,4,5,6-tetrahydropyrimidin-5-yl]-7-oxo-1-azabicyclo[3.2.0]hept-2-ene-2-carboxylic acid IR (Nujol): 1740, 1645, 1575 cm$^{-1}$.

NMR (D$_2$O, δ): 1.25 (3 H, d, J=5.8 Hz), 2.60–2.85 (2 H, m), 3.2–3.7 (5 H, m), 3.75–4.0 (3 H, m), 4.05–4.4 (2 H, m), 7.45–7.55 (1 H, m), 7.8–7.9 (1 H, m), 8.45–8.55 (2 H, m).

EXAMPLE 11-1)

To a solution of allyl (5R,6S)-3-[2-allyloxycarbonylamino-1-(N-allyloxycarbonylaminomethyl)ethyl]-6-[(1R)-1-hydroxyethyl]-7-oxo-1-azabicyclo[3.2.0]hept-2-ene-2-carboxylate (858 mg) in tetrahydrofuran (12 ml) and ethanol (4 ml) were added successively triphenylphosphine (0.19 g), acetic acid (0.10 ml) and tetrakis(triphenylphosphine)palladium (0.16 g) at room temperature under nitrogen. The temperature was raised to 30° C. and after all components were dissolved, tributyltin hydride (1.94 ml) was added dropwise. After stirring for 15 minutes at room temperature, ethyl acetate (50 ml) was added. After 30 minutes, the precipitate was filtrated and washed with ethyl acetate and dichloromethane under nitrogen, and dissolved in buffer solution (68 ml, pH 6.86). Ethyl 2-ethoxycarbonylacetoimidate hydrochloride (599 mg) was added to the solution at pH 8.5. After stirring for 30 minutes at pH 8.5. The mixture was stirred for 30 minutes at pH 7. After the starting material disappeared, the reaction mixture was washed five times with ethyl acetate-tetrahydrofuran (7:3, V/V, 70 ml) at pH 7. The aqueous layer was evaporated and the residue was purified by Diaion HP-20 column chromatography (eluent:acetonitrile-water=4:96, V/V) and silica gel column chlomatorgaphy (eluent:acetonitrile-water=100:00–85:15, V/V) to give (5R,6S)-6-[1R)-1-hydroxyethyl]-3-[2-(ethoxycarbonylmethyl)-3,4,5,6-tetrahydropyrimidin-5-yl]-7-oxo-1-azabicyclo[3.2.0]hept-2-ene-2-carboxylic acid (56.4 mg).

NMR (D$_2$O, δ): 1.28 (3 H, d, J=6.4 Hz), 1.29 (3 H, t, J=7.1 Hz), 2.90 (2 H, d, J=9.8 Hz), 3.35–3.56 (5 H, m), 3.80–3.95 (1 H, m), 4.15–4.31 (4 H, m).

EXAMPLE 11-2)

To a solution of allyl (5R,6S)-3-[2-allyloxycarbonylamino-1-(N-allyloxycarbonylaminomethyl)ethyl]-6-[(1R)-1-hydroxyethyl]-7-oxo-1-azabicyclo[3.2.0]hept-2-ene-2-carboxylate (988 mg) in tetrahydrofuran (12.4 ml) and ethanol (4.1 ml) were added successively triphenylphosphine (217 mg), 5,5-dimethyl-1,3-cyclohexanedione (1.16 g), acetic acid (0.12 ml) and tetrakis(triphenylphosphine)palladium (191 mg) at room temperature. The mixture was warmed to 30° C. and stirred for 5 minutes. Then the solution was cooled down to room temperature and stirred for 30 minutes to precipitate the solid. Ethyl acetate (33 ml) was added and the mixture was extracted twice with cold buffer (pH 6.86; 51 ml×1, 17 ml×1). The aqueous extracts were combined and the pH was adjusted to 7.0 with 10% aqueous potassium carbonate solution. The solution was cooled in an ice-bath and basified to pH 8.5. Ethyl 3-pentenimidate hydrochloride (508 mg) was added portionwise while adjusting pH to 8.5. After the addition, the solution was stirred at pH 8.5 for 10 minutes and at pH 7.0 for 50 minutes. The solution was washed five times with ethyl acetate-tetrahydrofuran (7:3, V/V, 55 ml) followed by adjusting to pH 7.0. The solution was concentrated to about 15 ml and chromatographed on Diaion HP-20 (eluent:acetonitrile-water=3:97-5:95, V/V) followed by silica gel (eluent:acetonitrile-water=100:0-70:30, V/V) to give (5R,6S)-6-[(1R)-1-hydroxyethyl]-3-[2-(2-butenyl)-1,4,5,6-tetrahydropyrimidin-5-yl]-7-oxo-1-azabicyclo[3.2.0]hept-2-ene-2-carboxylic acid (126 mg).

NMR ($D_2O$, δ): 1.28 (3 H, d, J=6.4 Hz), 1.72 (3 H, d, J=6.5 Hz), 2.87 (2 H, d, J=10.8 Hz), 3.18 (2 H, d, J=6.9 Hz), 3.28–3.56 (5 H, m), 3.76–3.89 (1 H, m), 4.10–4.29 (2 H, m), 5.39–5.54 (1 H, m), 5.76–5.93 (1 H, m).

The following compounds were obtained in substantially the same manner as that of Example 1.

EXAMPLE 11-3)

(5R,6S)-6-[(1R)-1-Hydroxyethyl]-3-[2-{(1-methyltetrazol-5-yl)thiomethyl}-1,4,5,6-tetrahydropyrimidin-5-yl]-7-oxo-1-azabicyclo[3.2.0]hept-2-ene-2-carboxylic acid NMR ($D_2O$, δ): 1.28 (3 H, d, J=6.3 Hz), 2.82 (2 H, d, J=10.0 Hz), 3.31–3.70 (5 H, m), 3.78–3.90 (1 H, m), 4.06 (3 H, s), 4.12–4.32 (2 H, m), 4.42 (2 H, s).

EXAMPLE 11-4)

(5R,6S)-6-[(1R)-1-Hydroxyethyl]-3-[2-(o-fluorobenzyl)-1,4,5,6-tetrahydropyrimidin-5-yl]-7-oxo-1-azabicicylo[3.2.0]hept-2-ene-2-carboxylic acid NMR ($D_2O$, δ): 1.26 (3 H, d, J=6.4 Hz), 2.70 (2 H, dd, J=8.5 Hz, 6.3 Hz), 3.26–3.60 (5 H, m), 3.75–3.87 (1 H, m), 3.85 (2 H, s), 4.07–4.20 (2 H, m), 7.14–7.23 (2 H, m), 7.34–7.41 (2 H, m).

EXAMPLE 11-5)

(5R,6S)-6-[(1R)-1-Hydroxyethyl]-3-[2-(2-methoxyacetamido)methyl-1,4,5,6-tetrahydropyrimidin-5-yl]-7-oxo-1-azabicyclo[3.2.0]hept-2-ene-2-carboxylic acid NMR ($D_2O$, δ): 1.28 (3 H, d, J=6.4 Hz), 2.88 (2 H, d, J=9.2 Hz), 3.36–3.60 (5 H, m), 3.46 (3 H, s), 3.75–3.90 (1 H, m), 4.11 (2 H, s), 4.15–4.26 (2 H, m), 4.28 (2 H, s).

EXAMPLE 11-6)

(5R,6S)-6-[(1R)-1-Hydroxyethyl]-3-[2-(methylthiomethyl)-1,4,5,6-tetrahydropyrimidin-5-yl]-7-oxo-1azabicyclo[3.2.0]hept-2-ene-2-carboxylic acid NMR ($D_2O$, δ): 1.28 (3 H, d, J=6.4 Hz), 2.17 (3 H, s), 2.90 (2 H, d, J=9.8 Hz), 3.35–3.62 (5 H, m), 3.55 (2 H, s), 3.80–3.87 (1 H, m), 4.13–4.26 (2 H, m).

EXAMPLE 11-7)

(5R,6S)-6-[(1R)-1-Hydroxyethyl]-3-[2-(2-methylthiazol-4-yl)methyl-1,4,5,6-tetrahydropyrimidin-5-yl]-7-oxo-1-azabicyclo[3.2.0]hept-2-ene-2-carboxylic acid NMR ($D_2O$, δ): 1.28 (3 H, d, J=6.4 Hz), 2.70 (3 H, s), 2.80 (2 H, dd, J=9.4 Hz, 3.8 Hz), 3.31–3.59 (5 H, m), 3.80–3.94 (1 H, m), 3.98 (2 H, s), 4.08–4.25 (2 H, m), 7.37 (1 H, s).

EXAMPLE 11-8)

(5R,6S)-6-[(1R)-1-Hydroxyethyl]-3-[2-(dimethylcarbamoyi)methyl-1,4,5,6-tetrahydropyrimidin-5-yl]-7-oxo-1-azabicyclo[3.2.0]hept-2-ene-2-carboxylic acid NMR ($D_2O$, δ): 1.29 (3 H, d, J=6.4 Hz), 2.91 (2 H, d, J=9.2 Hz), 2.97 (3 H, s), 3.08 (3 H, s), 3.39–3.55 (5 H, m), 3.75–3.90 (1 H, m), 4.10–4.25 (2 H, m).

EXAMPLE 11-9)

(5R,6S)-6-[(1R)-1-Hydroxyethyl]-3-[2-acetamidomethyl1,4,5,6-tetrahydropyrimidin-5-yl]-7-oxo-1-azabicyclo[3.2.0]hept-2-ene-2-carboxylic acid NMR ($D_2O$, δ): 1.28 (3 H, d, J=6.4 Hz), 2.09 (3 H, s), 2.88 (2 H, d, J=9.1 Hz), 3.35–3.52 (5 H, m), 3.75–3.90 (1 H, m), 4.17–4.26 (2 H, m), 4.20 (2 H, s).

EXAMPLE 11-10)

(5R,6S)-6-[(1R)-1-Hydroxyethyl]-3-[2-ureidomethyl-1,4,5,6-tetrahydropyrimidin-5-yl]-7-oxo-1-azabicyclo[3.2.0]hept-2-ene-2-carboxylic acid NMR ($D_2O$, δ): 1.28 (3 H, d, J=6.4 Hz), 2.88 (2 H, d, J=8.3 Hz), 3.40–3.65 (5 H, m), 3.80–3.90 (1 H, m), 4.13 (2 H, s), 4.10–4.25 (2 H, m).

EXAMPLE 11-11)

(5R,6S)-6-[(1R)-1-Hydroxyethyl]-3-[2-hydroxymethyl-1,4,5,6-tetrahydropyrimidin-5-yl]-7-oxo-1-azabicyclo[3.2.0]hept-2-ene-2-carboxylic acid NMR ($D_2O$, δ): 1.28 (3 H, d, J=6.4 Hz), 2.89 (2 H, d, J=10.0 Hz), 3.37–3.57 (5 H, m), 3.80–3.95 (1 H, m), 4.13–4.26 (2 H, m), 4.43 (2 H, s).

EXAMPLE 11-12)

(5R,6S)-6-[(1R)-1-Hydroxyethyl]-3-[2-(N-ethylcarbamoyloxymethyl)-1,4,5,6-tetrahydropyrimidin-5-yl]-7-oxo-1-azabicyclo[3.2.0]hept-2-ene-2-carboxylic acid NMR ($D_2O$, δ): 1.12 (3 H, t, J=7.3 Hz), 1.28 (3 H, d, J=6.4 Hz), 2.88 (2 H, d, J=9.1 Hz), 3.17 (2 H, q, J=7.3 Hz), 3.38–3.60 (6 H, m), 3.75–3.90 (1 H, m), 4.10–4.35 (3 H, m).

EXAMPLE 12-1)

(5R,6S)-6-[(1R)-1-Hydroxyethyl]-3-[2-{2-(pyridin-3-yl)vinyl}-1,4,5,6-tetrahydropyrimidin-5--Yl]-7-oxo-1-azabicyclo[3.2.0]hept-2-ene-2-carboxylic acid IR (Nujol): 1740, 1620, 1580 cm$^{-1}$.

NMR ($D_2O$, δ): 1.29 (3 H, d, J=6.4 Hz), 2.92 (2 H, d, J=16 Hz), 7.53 (1 H, d, J=16 Hz), 7.40–7.70 (1 H, m), 8.09–8.14 (1 H, m), 8.50–8.72 (2 H, m).

EXAMPLE 12-2)

(5R,6S)-6-[(1R)-1-Hydroxyethyl]-3-[2-(2-methylpyridin-3-yl)methyl-1,4,5,6-tetrahydropyrimidin-5-yl-]-7-oxo-1-azabicyclo[3.2.0]hept-2-ene-2-carboxylic acid IR (Nujol): 1740, 1650, 1605, 1580 cm$^{-1}$.

NMR (D₂O, δ): 1.28 (3 H, d, J=6.33 Hz), 2.49 (3 H, s),
2.84 (2 H, d, J=10.1 Hz), 3.30-4.30 (8 H, m), 4.00 (2 H, s), 7.30-7.40 (1 H, m), 7.70-7.80 (1 H, m), 8.40-8.50 (2 H, m).

EXAMPLE 12-3)

(5R,6S)-6-[(1R)-1-Hydroxyethyl]-3-(2-{2-(pyridin-3-yl)ethyl}-1,4,5,6-tetrahydropirimidin-5-yl]-7-oxo-1-azabicyclo[3.2.0]hept-2-ene-2-carboxylic acid IR (Nujol): 1740, 1630, 1580 cm⁻¹.

NMR (D₂O, δ): 1.28 (3 H, d, J=6.37 Hz), 2.75-3.50 (11 H, m), 3.60-3.80 (1 H, m), 4.05-4.25 (2 H, m), 7.43-7.50 (1 H, m), 7.75-7.79 (1 H, m), 8.43-8.47 (2 H, m).

EXAMPLE 12-4)

(5R,6S)-6-[(1R)-1-Hydroxyethyl]-3-{2-(2-pyridylmethyl)-1,4,5,6-tetrahydropyrimidin-5-yl]-7-oxo-1-azabicyclo[3.2.0]hept-2-ene-2-carboxylic acid IR (Nujol): 1750, 1645, 1580 cm⁻¹.

NMR (D₂O, δ): 1.27 (3 H, d, J=6.38 Hz), 2.70-2.85 (2 H, m), 3.29-4.25 (8 H, m), 4.05 (2 H, s), 7.42-7.50 (2 H, m), 7.87-7.95 (1 H, m), 8.50-8.56 (1 H, m).

EXAMPLE 13-1)

To a solution of allyl (5R,6S)-3-[2-allyloxycarbonylamino-1-(N-allyloxycarbonylaminomethyl)ethyl]-6-[(1R)-1-hydroxyethyl]-7-oxo-1-azabicyclo[3.2.0]hept-2-ene-2-carboxylate (1.0 g) in tetrahydrofuran (12.5 ml) and ethanol (4.2 ml) were added successively triphenyl phosphine (0.22 g), acetic acid (0.72 ml) and tetrakis(triphenylphosphine)palladium (0.20 g) at room temperature under nitrogen. The temperature was raised to 30° C. and after all components were dissolved, tributyltin hydride (2.25 ml) was added dropwise. After stirring for 15 minutes at room temperature, 30 ml of ethyl acetate was added. After 30 minutes, the precipitate was filtered and washed with ethyl acetate and dichloromethane under nitrogen, and dissolved in buffer solution (40 ml, pH 6.86). Ethyl 4-(3-methylimidazolio)-butanimidate bromide hydrochloride was added to the solution at pH 8.5. After stirring for 30 minutes at pH 8.5, the mixture was stirred for 30 minutes at pH 7, and washed with a mixture of ethyl acetate and tetrahydrofuran (7:3, 50 ml×4). Evaporation of the solvent gave a residue which was chromatographed on Chromatorex DM1020T (trademark, Fuji-Davison Chemical Ltd., 150 ml) eluting with water. The fractions containing the object compound were collected and passed through Amberlyst A-26 (Cl form, 25 ml) (trademark, Rohm & Haas Co.), and evaporated. Lyophilization of the residue gave (5R,6S)-6-[(1R)-1hydroxyethyl]-3-[2-{3-(3-methylimidazolio)propyl}-1,4,5,6-tetrahydropyrimidin-5-yl]-7-oxo-1-azabicyclo[3.2.0]hept-2-ene-2-carboxylic acid chloride (120 mg).

IR (Nujol) 3300, 1750, 1620, 1580 cm⁻¹.

NMR (D₂O, δ): 1.28 (3 H, d, J=6 Hz), 2.05-4.45 (16 H, m), 3.91 (3 H, s), 7.40-7.55 (2 H, m), 8.68-8.90 (1 H, m).

The following compound was obtained in substantially the same manner as that of Example 13-1).

EXAMPLE 13-2)

(5R,6S)-6-[(1R)-1-Hydroxyethyl]-3-[2-{(1-methyl-3-pyridinio)methyl) -1,4,5,6-tetrahydropyrimidin-5-yl]-7-oxo-1-azabicyclo[3.2.0]hept-2-ene-2-carboxylic acid chloride IR (Nujol): 3400, 1750, 1640 cm⁻¹.

NMR (D₂O, δ): 1.28 (3 H, d, J=6 Hz), 2.87 (2 H, d, J=10 Hz), 3.05-4.00 (6 H, m), 4.02-4.30 (4 H, m), 4.42 (3 H, s), 8.02-8.20 (1 H, m), 8.40-8.62 (1 H, m), 8.70-9.05 (2 H, m).

The following compounds were obtained in substantially the same manner as that of Example 11-2).

EXAMPLE 13-3)

(5R,6S)-3-[2-(Imidazol-4-ylmethyl)-1,4,5,6-tetrahydropyrimidin-5-yl]-6-[(1R)-1-hydroxymethyl]-7-oxo-1-azabicyclo[3.2.0]hept-2-ene-2-carboxylic acid IR (Nujol): 3200, 1760, 1660, 1630, 1580 cm⁻¹.

NMR (D₂O, δ): 1.28 (3 H, d, J=6 Hz), 2.70-2.95 (2 H, m), 3.22-3.61 (5 H, m), 3.65-4.02 (3 H, m), 4.02-4.26 (2 H, m), 7.19 (1 H, s), 7.77 (1 H, s).

EXAMPLE 13-4)

(5R,6S)-3-[2-(Imidazol-2-ylmethyl)-1,4,5,6-tetrahydropyrimidin-5-yl]-6-[(1R)-1-hydroxyethyl]-7-oxo-1-azabicyclo[3.2.0]hept-2-ene-2-carboxylic acid IR (Nujol): 3200, 1750, 1660, 1580 cm⁻¹.

NMR (D₂O, δ): 1.28 (3 H, d, J=6 Hz), 2.70-3.10 (2 H, m), 3.10-3.70 (5 H, m), 3.70-4.00 (1 H, m), 4.04 (2 H, s), 4.05-4.40 (2 H, m), 7.12 (2 H, s).

EXAMPLE 13-5)

(5R,6S)-3-[2-(Difluoromethylthiomethyl)-1,4,5,6-tetrahydropyrimidin-5-yl]-6-[(1R)-1-hydroxyethyl]-7-oxo-1-azabicyclo[3.2.0]hept-2-ene-2-carboxylic acid IR (Nujol): 3150, 1760, 1660, 1630, 1580 cm⁻¹.

NMR (D₂O, δ): 1.28 (3 H, d, J=6 Hz), 2.88 (2 H, d, J=10 Hz), 3.30-3.65 (5 H, m), 3.70-3.96 (3 H, m), 4.08-4.27 (2 H, m), 7.14 (1 H, t, J=55 Hz).

What is claimed is:

1. A compound of the formula:

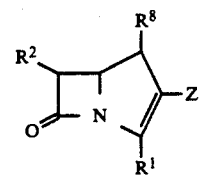

in which
R¹ is carboxy, COO⁻ or protected carboxy,
R² is hydroxy(lower)alkyl or protected hydroxy(lower)alkyl,
R⁸ is hydrogen or lower alkyl,
Z is a group of the formula:

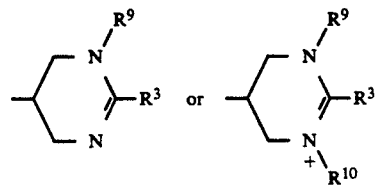

wherein
R³ is hydrogen; lower alkyl or lower alkenyl, each of which is optionally substituted by the group consisting of lower alkoxy, carbamoyl, hydroxy, halogen, mono(or di)(lower)alkylcarbamoyl, mono(or di)(lower)alkenylcarbamoyl, mono(or bis)carbamoyl, optionally substituted cyclicaminocarbonyl, acylamino, ureido, optionally substituted heterocyclic-carbonylamino, carbamoyloxy, mono(or di)(lower)alkylcarbamoyloxy, lower alkylthio, halo(lower)alkylthio, optionally substituted heterocyclicthio, optionally substituted heterocyclic group, optionally substituted aryl, and acyl;

$R^9$ is hydrogen or lower alkyl, and $R^{10}$ is lower alkyl, or a pharmaceutically acceptable salt thereof.

2. The compound of claim 1, wherein $R^1$ is carboxy, COO⁻ or esterified carboxy, $R^2$ is hydroxy(lower)alkyl, acyloxy(lower)alkyl, ar(lower)alkyloxy(lower)alkyl, tri(lower)alkylsilyloxy(lower)alkyl, triarylsilyloxy(lower)alkyl or triar(lower)alkylsilyloxy(lower)alkyl, and $R^3$ is hydrogen; lower alkyl lower alkenyl; lower alkoxy(lower)alkyl; carbamoyl(lower)alkyl; hydroxy(lower)alkyl; halo(lower)alkyl; mono(or di)(lower)alkylcarbamoyl(lower)alkyl; mono(or di)(lower)alkenylcarbamoyl(lower)alkyl; mono(or bis)carbamoyl(lower)alkyl; lower alkyleneaminocarbonyl(lower)alkyl optionally substituted by one or two suitable substitutent(s) selected from the group consisting of lower alkyl, amino, nitro, hydroxy and halogen; lower alkanoylamino(lower)alkyl; lower alkylsulfonylamino(lower)alkyl; lower alkoxycarbonylamino(lower)alkyl; lower alkoxy(lower)alkanoylamino(lower)alkyl; ureido(lower)alkyl; heterocyclic-carbonylamino(lower)alkyl, wherein the heterocyclic moiety is unsaturated 5 or 6-membered heteromonocyclic group containing 1 to 4 nitrogen atom(s) optionally substituted by one or two suitable substituent(s) selected from the group consisting of hydroxy, tri(lower)alkylsilyloxy, hydroxy(lower)alkyl, tri(lower)alkylsilyloxy(lower)alkyl, halogen, lower alkoxy, lower alkyl, lower alkoxy(lower)alkyl, lower alkylthio and imino-protective group; carbamoyloxy(lower)alkyl; mono(or di)(lower)alkylcarbamoyloxy(lower)alkyl; lower alkylthio(lower)alkyl; mono(or di)halo(lower)alkylthio(lower)alkyl; heterocyclicthio(lower)alkyl, wherein the heterocyclic moiety is unsaturated 5 or 6-membered heteromonocyclic group containing 1 to 4 nitrogen atom(s), or containing 1 to 2 sulfur atom(s) and 1 to 3 nitrogen atom(s), and each of which is optionally substituted by one or two suitable substituent(s) selected from the group consisting of hydroxy, tri(lower)alkylsilyloxy, hydroxy(lower)alkyl, tri(lower)alkylsilyloxy(lower)alkyl, halogen, lower alkoxy, lower alkyl, lower alkoxy(lower)alkyl, lower alkylthio and imino-protective group; heterocyclic(lower)alkyl, wherein the heterocyclic moiety is unsaturated 5 or 6-membered heteromonocyclic group containing 1 to 4 nitrogen atom(s), or containing 1 to 2 sulfur atom(s) and 1 to 3 nitrogen atom(s), and each of which is optionally substituted by one or two suitable substituent(s) selected from the group consisting of hydroxy, tri(lower)alkylsilyloxy, hydroxy(lower)alkyl, tri(lower)alkylsilyloxy(lower)alkyl, halogen, lower alkoxy, lower alkyl, lower alkoxy(lower)alkyl, lower alkylthio and imino-protective group; phenyl(lower)alkyl optionally substituted by one or two suitable substituent(s) selected from the group consisting of hydroxy, tri(lower)alkylsilyloxy, hydroxy(lower)alkyl, tri(lower)alkylsilyloxy(lower)alkyl, halogen, lower alkoxy, lower alkyl, lower alkoxy(lower)alkyl, lower alkylthio and imino-protective group; or lower alkoxycarbonyl(lower)alkyl.

3. The compound of claim 1, wherein $R^1$ is carboxy, COO⁻ or lower alkenyloxycarbonyl, $R^2$ is hydroxy(lower)alkyl or tri(lower)alkylsilyloxy(lower)alkyl, and $R^3$ is hydrogen; lower alkyl; lower alkenyl; lower alkoxy(lower)alkyl; carbamoyl(lower)alkyl; hydroxy(lower)alkyl; halo(lower)alkyl; mono(or di)(lower)alkylcarbamoyl(lower)alkyl; mono(or di)(lower)alkenylcarbamoyl(lower)alkyl; mono(or bis)carbamoyl(lower)alkyl; lower alkyleneaminocarbonyl(lower)alkyl optionally substituted by one or two suitable substituent(s) selected from the group consisting of lower alkyl, amino, nitro, hydroxy and halogen; lower alkanoylamino(lower)alkyl; lower alkylsulfonylamino(lower)alkyl; lower alkoxycarbonylamino(lower)alkyl; lower alkoxy(lower)alkanoylamino(lower)alkyl; ureido(lower)alkyl; heterocyclic-carbonylamino(lower)alkyl, wherein the heterocyclic moiety is pyrrolyl, pyrrolinyl, imidazolyl, pyrazolyl, pyridyl, pyridyl N-oxide, pyrimidyl, pyrazinyl, pyridazinyl, triazolyl, tetrazolyl or dihydrotriazinyl and is optionally substituted by one or two suitable substituent(s) selected from the group consisting of hydroxy, tri(lower)alkylsilyloxy, hydroxy(lower)alkyl, tri(lower)alkylsilyloxy(lower)alkyl, halogen, lower alkoxy, lower alkyl, lower alkoxy(lower)alkyl, lower alkylthio and imino-protective group; carbamoyloxy(lower)alkyl; mono(or di)(lower)alkylcarbamoyloxy(lower)alkyl; lower alkylthio(lower)alkyl; mono(or di)halo(lower)alkylthio(lower)alkyl; heterocyclicthio(lower)alkyl, wherein the heterocyclic moiety is pyrrolyl, pyrrolinyl, imidazolyl, pyrazolyl, pyridyl, pyridyl, N-oxide, pyrimidyl, pyrazinyl, pyridazinyl, triazolyl, tetrazolyl, dihydrotriazinyl, thiazolyl, 1,2-thiazolyl, thiazolinyl or thiadiazolyl, and is optionally substituted by one or two suitable substituent(s) selected from the group consisting of hydroxy, tri(lower)alkylsilyloxy, hydroxy(lower)alkyl, tri(lower)alkylsilyloxy(lower)alkyl, halogen, lower alkoxy, lower alkyl, lower alkoxy(lower)alkyl, lower alkylthio and imino-protective group; heterocyclic(lower)alkyl, wherein the heterocyclic moiety is pyrrolyl, pyrrolinyl, imidazolyl, pyrazolyl, pyridyl, pyridyl N-oxide, pyrimidyl, pyrazinyl, pyridazinyl, triazolyl, tetrazolyl, dihydrotriazinyl, thiazolyl, 1,2-thiazolyl, thiazolinyl or thiadiazolyl, and is optionally substituted by one or two suitable substituent(s) selected from the group consisting of hydroxy, tri(lower)alkylsilyloxy, hydroxy(lower)alkyl, tri(lower)alkylsilyloxy(lower)alkyl, halogen, lower alkoxy, lower alkyl, lower alkoxy(lower)alkyl, lower alkylthio and imino-protective group; phenyl(lower)alkyl optionally substituted by one or two suitable substituent(s) selected from the group consisting of hydroxy, tri(lower)alkylsilyloxy, hydroxy(lower)alkyl, tri(lower)alkylsilyloxy(lower)alkyl, halogen, lower alkoxy, lower alkyl, lower alkoxy(lower)alkyl, lower alkylthio and imino-protective group; or lower alkoxycarbonyl(lower)alkyl.

4. The compound of claim 3, wherein
$R^1$ is carboxy or COO−,
$R^2$ is hydroxy(lower)alkyl, and
$R^3$ is hydrogen; lower alkyl; lower alkenyl; lower alkoxy(lower)alkyl; carbamoyl(lower)alkyl; hydroxy(lower)alkyl; halo(lower)alkyl; mono(or di)(lower)alkylcarbamoyl(lower)alkyl; mono(or di)(lower)alkenylcarbamoyl(lower)alkyl; mono(or bis)carbamoyl(lower)alkyl; lower alkyleneaminocarbonyl(lower)alkyl optionally substituted by hydroxy, lower alkanoylamino(lower)alkyl; lower alkylsulfonylamino(lower)alkyl; lower alkoxycarbonylamino(lower)alkyl; lower alkoxy(lower)alkanoylamino(lower)alkyl; ureido(lower)alkyl; pyridylcarbonylamino(lower)alkyl optionally substituted by lower alkylthio, carbamoyloxy(lower)alkyl; mono(or di)(lower)alkylcarbamoyloxy(lower)alkyl; lower alkylthio(lower)alkyl; mono(or di)halo(lower)alkylthio(lower)alkyl; imidazolylthio(lower)alkyl, tetrazolylthio(lower)alkyl or thiadiazolylthio(lower)alkyl, each of which is optionally substituted by lower alkyl; pyridyl(lower)alkyl, imidazolyl(lower)alkyl or thiazolyl(lower)alkyl, each of which is optionally substituted by lower alkyl; phenyl(lower)alkyl optionally substituted by halogen, or lower alkoxycarbonyl(lower)alkyl.

5. The compound of claim 4, wherein
$R^2$ is hydroxy($C_1$-$C_4$)alkyl,
$R^8$ is hydrogen or $C_1$-$C_4$ alkyl,
$R^3$ is hydrogen; $C_1$-$C_4$ alkyl; $C_2$-$C_6$ alkenyl; $C_1$-$C_4$ alkoxy($C_1$-$C_4$)alkyl; carbamoyl($C_1$-$C_4$)alkyl; hydroxy($C_1$-$C_4$)alkyl; halo($C_1$-$C_4$)alkyl; mono(or di)($C_1$-$C_4$)alkylcarbamoyl(lower)alkyl; mono($C_2$-$C_4$)alkenylcarbamoyl($C_1$-$C_4$)alkyl; monocarbamoyl($C_1$-$C_4$)alkyl; $C_3$-$C_6$ alkyleneaminocarbonyl( )alkyl optionally substituted by hydroxy; $C_1$-$C_4$ alkanoylamino($C_1$-$C_4$)alkyl; $C_1$-$C_4$ alkylsulfonylamino($C_1$-$C_4$)alkyl; $C_1$-$C_4$ alkoxycarbonylamino($C_1$-$C_4$)alkyl; $C_1$-$C_4$ alkoxy($C_1$-$C_4$)alkanoylamino($C_1$-$C_4$)alkyl; ureido($C_1$-$C_4$)alkyl; pyridylcarbonylamino($C_1$-$C_4$)alkyl optionally substituted by $C_1$-$C_4$ alkylthio; carbamoyloxy($C_1$-$C_4$)alkyl; mono($C_1$-$C_4$)alkylcarbamoyloxy($C_1$-$C_4$)alkyl; $C_1$-$C_4$ alkylthio($C_1$-$C_4$)alkyl; halo($C_1$-$C_4$)alkylthio($C_1$-$C_4$)alkyl; imidazolylthio($C_1$-$C_4$)alkyl, tetrazolylthio($C_1$-$C_4$)alkyl or thiadiazolylthio($C_1$-$C_4$)alkyl, each of which is optionally substituted by $C_1$-$C_4$ alkyl; pyridyl($C_1$-$C_4$)alkyl, imidazolyl($C_1$-$C_4$)alkyl or optionally substituted by $C_1$-$C_4$ alkyl; phenyl($C_1$-$C_4$)alkyl optionally substituted by halogen, or $C_1$-$C_4$ alkoxycarbonyl($C_1$-$C_4$)alkyl;
$R^9$ is hydrogen or $C_1$-$C_4$ alkyl, and
$R^{10}$ is $C_1$-$C_4$ alkyl.

6. The compound of claim 5, wherein
$R^2$ is 1-hydroxyethyl,
$R^8$ is hydrogen,
$R^3$ is hydrogen; methyl; vinyl, 2-butenyl; methoxymethyl; carbamoylmethyl; hydroxymethyl, 2-hydroxyethyl; chloromethyl; methylcarbamoylmethyl, dimethylcarbamoylmethyl; allylcarbamoylmethyl; N-(2-hydroxyethyl)carbamoylmethyl; 3-hydroxyazetidin-1-ylcarbonylmethyl; acetamidomethyl; methylsulfonylaminomethyl; methoxycarbonylaminomethyl; methoxyacetylaminomethyl; ureidomethyl; pyridin-3-ylcarbonylaminomethyl, 2-methylthiopyridin-3-ylcarbonylaminomethyl; carbamoyloxymethyl; methylcarbamoyloxymethyl, ethylcarbamoyloxymethyl; methylthiomethyl; difluoromethylthiomethyl; (1-methyltetrazol-5-ylthio)methyl, imidazol-2-ylthiomethyl, (1-methylimidazol-2-ylthio)methyl, 1,2,3-thiadiazol-5-ylthiomethyl, pyridin-2(or 3)-ylmethyl, 2-methylpyridin-3-ylmethyl, imidazol-2(or 4)-ylmethyl, 3-(imidazol-1-yl)propyl, 2-(2-methylthiazol-4-yl)ethyl, 2-(pyridin-3-yl)vinyl; 4-fluorophenylmethyl or ethoxycarbonylmethyl;
$R^9$ is hydrogen or methyl, and
$R^{10}$ is methyl.

7. A pharmaceutical composition which comprises a compound of claim 1 or a pharmaceutically acceptable salt thereof and a pharmaceutically acceptable carrier or excipient.

8. A process for preparing a pharmaceutical composition which comprises admixing a compound of claim 1 or a pharmaceutically acceptable salt thereof with a pharmaceutically acceptable carrier or excipient.

9. A method for treating infectious diseases which comprises administering an effective amount of the compound of claim 1 or a pharmaceutically acceptable salt thereof to a human or animal in need thereof.

* * * * *